(12) United States Patent
Qian et al.

(10) Patent No.: US 11,905,230 B2
(45) Date of Patent: Feb. 20, 2024

(54) PHENOXYACETIC ACID DERIVATIVES, PREPARATION METHOD THEREOF AND USE THEREOF AS MEDICAMENT

(71) Applicant: CHINA PHARMACEUTICAL UNIVERSITY, Nanjing (CN)

(72) Inventors: Hai Qian, Nanjing (CN); Wenlong Huang, Nanjing (CN); Chunxia Liu, Nanjing (CN); Jianyong Yang, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 55 days.

(21) Appl. No.: 16/617,409

(22) PCT Filed: May 24, 2018

(86) PCT No.: PCT/CN2018/088204
§ 371 (c)(1),
(2) Date: Nov. 26, 2019

(87) PCT Pub. No.: WO2018/219204
PCT Pub. Date: Dec. 6, 2018

(65) Prior Publication Data
US 2021/0122704 A1 Apr. 29, 2021

(30) Foreign Application Priority Data
May 27, 2017 (CN) .......................... 201710407580.X

(51) Int. Cl.
*C07C 229/42* (2006.01)
*C07C 255/49* (2006.01)
*C07C 317/28* (2006.01)
*C07D 261/08* (2006.01)
*C07C 255/59* (2006.01)

(52) U.S. Cl.
CPC .......... *C07C 229/42* (2013.01); *C07C 255/59* (2013.01); *C07C 317/28* (2013.01); *C07D 261/08* (2013.01)

(58) Field of Classification Search
CPC ........................... C07C 229/42; C07C 255/59
See application file for complete search history.

(56) References Cited

U.S. PATENT DOCUMENTS

2008/0269220 A1* 10/2008 Yasuma .................... A61P 3/04
514/237.5

FOREIGN PATENT DOCUMENTS

CN          104326950       * 10/2014  .......... C07C 317/18
WO  WO-2004007439 A1 *  1/2004  .......... A61K 31/165

OTHER PUBLICATIONS

CN104326950 downloaded from Google Patents on Mar. 23, 2023.*
WO2004007439A1—English Translation (Year: 2023).*
9(9) ACS Med Chem Lett. 870-871 (2018) (Year: 2018).*

* cited by examiner

*Primary Examiner* — Brandon J Fetterolf
*Assistant Examiner* — Frank S. Hou
(74) *Attorney, Agent, or Firm* — CBM PATENT CONSULTING, LLC

(57) ABSTRACT

The present invention relates to a novel phenoxyacetic acid derivative represented by the general formula (I), preparation method thereof and use of a pharmaceutical composition containing the derivative in preparing a medicament for treating diabetes and metabolic syndrome. The phenoxyacetic acid derivatives have excellent in vivo hypoglycemic activity, which can be used for preventing or treating diabetes.

2 Claims, 1 Drawing Sheet

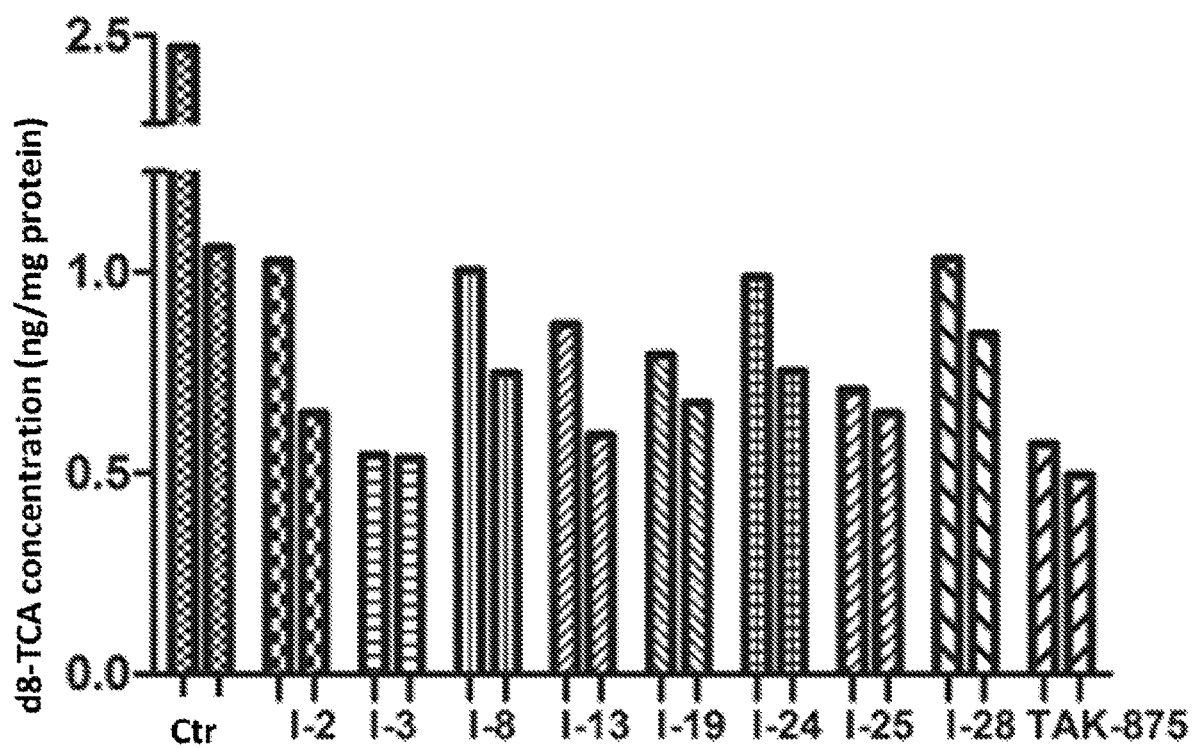

PHENOXYACETIC ACID DERIVATIVES, PREPARATION METHOD THEREOF AND USE THEREOF AS MEDICAMENT

TECHNICAL FIELD

The present invention relates to the field of pharmacology related to diabetes, and in particular to a novel phenoxyacetic acid derivative, preparation method thereof and use of the pharmaceutical composition containing the derivative in preparing a medicament for treating diabetes and metabolic syndrome. The structure of the phenoxyacetic acid derivative involved in the present invention is unique and novel in structural modification of the class of compounds.

BACKGROUND

Diabetes is an energy metabolism disease, it can be divided into type I diabetes (insulin-dependent diabetes) and type II diabetes (non-insulin-dependent diabetes). There are currently 366 million people with diabetes in the world, accounting for 6.4% of the world's population, in which 90-95% of the total number of diabetic patients belong to type II diabetes.

Diabetes can be treated with diet and exercise. When these can not alleviate the symptoms, medication is needed. At present, the treatment medicines of diabetes include: biguanides such as metformin, which can reduce the production of glucose in the liver; sulfonylureas such as glibenclamide, which can stimulate the pancreatic β cells to secrete more insulin; thiazolidinediones such as pegetaline ketones, which can enhance the bioavailability of insulin by activating the protonase proliferator-activated receptor gamma (PPAR-γ); α-glucosidase inhibitors such as acarbose, which can inhibit the production of glucose in the guts; glucagon-like peptide-1 (GLP-1) analogues such as liraglutide, which can promote the secretion of insulin from β cells of the pancreas; dipeptidyl peptidase IV (DPP-IV) inhibitors such as sitagliptin, which can inhibit degradation of GLP-1 in vivo. However, the current methods for treating diabetes have certain drawbacks: for example, insulin injections and sulfonylureas may cause side effects of hypoglycemia and weight gain; metformins, alpha-glucosidase inhibitors and GLP-1 analogues may cause side effects on gastrointestinal track; PPAR-γ agonists may cause side effects of weight gain and edema; DPP-IV inhibitors may cause side effects of pharyngitis, headaches and infection. Research is ongoing in a number of areas to bring about new safer and more effective hypoglycemic drugs.

Free fatty acid receptors (FFARs) are G protein-coupled receptors (GPCRs) that have been orphaned in recent years. The currently identified free fatty acid receptors are G-protein coupled receptor 40 (GPR40) family, including GPR40 (also known as free fatty acid receptor 1, FFA1), GPR41 (also known as free fatty acid receptor 3, FFA3), GPR43 (also known as free fatty acid receptor 2, FFA2) and other families of GPR84 and GPR120. GPR40 is an orphan-type GPCR found in the search for a new growth hormone neuropeptide-galanin receptor (GALR) subtype, highly expressed in pancreatic beta cells and insulin-secreting cell lines. GPR40 can combine a variety of fatty acids in plasma such as palmitic acid, stearic acid, oleic acid, linoleic acid and linolenic acid to achieve physiological functions. For example, long-chain free fatty acids are activated by binding to GPR40, which induces an increase in intracellular calcium levels and enhances glucose-stimulated insulin secretion (GSIS). The GPR40 modulator acts as an incretin to promote GEI and can also be used in combination with a variety of therapeutic diabetes drugs. Based on the above, GPR40 agonists can treat diabetes and related indications, especially type II diabetes, obesity insulin resistance, glucose intolerance, and other metabolic syndrome conditions. With GPR40 as a potential therapeutic target, the discovery and modification of compounds with GPR40 agonistic activity has important research value and application prospects.

A series of patent applications for GPR40 agonists have been disclosed, including WO2004041266, WO2005087710, WO2005051890, WO2006083781, WO2007013689, WO2008066097, WO2009054390, WO2010085525, WO2015024448, WO2015088868, etc.

The present invention relates to novel phenoxyacetic acid derivatives having excellent GPR40 agonistic activity and hypoglycemic activity in vivo, low hepatotoxicity and high GPR40 selective agonistic activity. Therefore, the phenoxyacetic acid derivatives and pharmaceutically acceptable salts thereof are potentially useful for the treatment or prevention of diabetes and related diseases.

SUMMARY OF INVENTION

One object of the present invention is to provide a compound of the formula (I) or a pharmaceutically acceptable salt thereof:

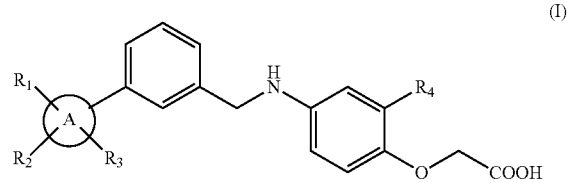

(I)

wherein, ring A is selected from aryl or heteroaryl;

$R_1$, $R_2$ and $R_3$ are each independently selected from the group consisting of hydrogen, halogen, hydroxy, cyano, alkyl, alkoxy, wherein the alkyl or alkoxy is optionally further substituted by one or more group selected from the group consisting of halogen, hydroxy, cyano, alkyl and alkoxy.

$R_4$ is selected from the group consisting of hydrogen and halogen.

In a preferred embodiment of the present invention, a compound represented by the following formula (I) or a pharmaceutically acceptable salt thereof is preferred:

wherein, ring A is preferably selected from benzene ring or isoxazole ring;

$R_1$, $R_2$ and $R_3$ are each independently selected from the group consisting of hydrogen, halogen, hydroxy, cyano, alkyl, alkoxy, wherein the alkyl or alkoxy is optionally further substituted by one or more group selected from the group consisting of halogen, hydroxy, cyano, alkyl and alkoxy.

$R_4$ is selected from the group consisting of hydrogen and halogen.

Provided are further preferred compounds of the formula (I) or pharmaceutically acceptable salts thereof:

wherein, ring A is preferably selected from benzene ring or isoxazole ring;

$R_1$, $R_2$ and $R_3$ are each independently selected from the group consisting of hydrogen, halogen, hydroxy, cyano, $C_1$-$C_6$ alkyl, $C_1$-$C_6$ alkoxy, wherein said $C_1$-$C_6$ alkyl or $C_1$-$C_6$ alkoxy is optionally substituted by one or more group selected from the group consisting of halogen, hydroxy, cyano, alkyl, alkoxy; said $C_1$-$C_6$ alkyl is selected from the group consisting of methyl, ethyl, propyl, isopropyl, n-butyl, isobutyl, tert-butyl, n-pentyl, isopentyl, neopentyl, n-hexyl, isohexyl, cyclohexyl; said $C_1$-$C_6$ alkoxy is selected from the group consisting of methoxy, ethoxy, propoxy, isopropoxy, n-butoxy, isobutoxy, tert-butoxy, n-pentyloxy, isopentyloxy, neopentyloxy, n-hexyloxy, isohexyloxy and cyclohexyloxy.

$R_4$ is preferably selected from hydrogen and F.

Provided are more preferred compounds of the formula (I) or pharmaceutically acceptable salts thereof:
wherein:
ring A is preferably derived from a benzene ring or an isoxazole ring;
$R_1$, $R_2$ and $R_3$ are each independently selected from the group consisting of hydrogen, F, Cl, cyano, $C_1$-$C_3$ alkyl, $C_1$-$C_3$ alkoxy, wherein said $C_1$-$C_3$ alkyl or $C_1$-$C_3$ alkoxy is optionally substituted by one or more group selected from the group consisting of F, hydroxy, cyano, $C_1$-$C_3$ alkyl, $C_1$-$C_3$ alkoxy; wherein said $C_1$-$C_3$ alkyl is selected from the group consisting of methyl, ethyl, propyl or isopropyl; said $C_1$-$C_3$ alkoxy is selected from the group consisting of methoxy, ethoxy, propoxy and isopropoxy;
$R_4$ is preferably selected from hydrogen and F.

Provided are still further preferred compounds of the formula (I) or pharmaceutically acceptable salts thereof:
wherein:
ring A is preferably selected from a benzene ring or:

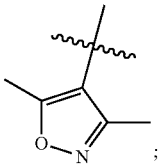

$R_1$ is selected from the group consisting of methyl and hydrogen, $R_2$ is selected from the group consisting of ethoxy, propoxy, methyl, methylsulfonylpropoxy, methoxyethoxy and hydrogen, and $R_3$ is selected from the group consisting of methyl, trifluoromethyl, F, Cl, isopropyl, cyano, methoxy, hydrogen, and $R_4$ is selected from the group consisting of hydrogen and F.

The compounds represented by the formula (I) or pharmaceutically acceptable salts thereof of the present invention are preferably any of the following compounds:
2-(4-((4'-ethoxy-2',6'-dimethyl-[1,1'-biphenyl]-3-methylene)amino)-2-fluorophenoxy)acetic acid (I-1);
2-(4-((2'-chloro-[1,1'-biphenyl]-3-methylene)amino)-2-fluorophenoxy)acetic acid (I-2);
2-(4-((2'-methyl-[1,1'-biphenyl]-3-methylene)amino)-2-fluorophenoxy)acetic acid (I-3);
2-(4-((2'-fluoro-[1,1'-biphenyl]-3-methylene)amino)-2-fluorophenoxy)acetic acid (I-4)
2-(4-((2'-chloro-4'-methyl-[1,1-biphenyl]-3-methyl ene)amino)-2-fluorophenoxy)acetic acid (I-5)
2-(4-((2'-methoxy-[1,1'-biphenyl]-3-methylene)amino)-2-fluorophenoxy)acetic acid (I-6)
2-(4-((2'-nitrile-[1,1'-biphenyl]-3-methylene)amino)-2-fluorophenoxy)acetic acid (I-7)
2-(4-((2'-trifluoromethyl-[1,1'-biphenyl]-3-methylene)amino)-2-fluorophenoxy)acetic acid (I-8)
2-(4-((4'-propoxy-2',6'-dimethyl-[1,1'-biphenyl]-3-methylene)amino)-2-fluorophenoxy)acetic acid (I-9);
2-(2-fluoro-4-((4'-(2-methoxyethoxy)-2',6'-dimethyl-[1,1'-biphenyl]-3-methylene)amino)phenoxy)acetic acid (I-10)
2-(4-(([1,1'-biphenyl]-3-methylene)amino)-2-fluorophenoxy)acetic acid (I-11)
2-(4-((2',6'-dimethyl-4'-(3-(methylsulfonyl)propoxy)-[1,1'-biphenyl]-3-methylene)amino)-2-fluorophenoxy)acetic acid (I-12)
2-(4-((4'-ethoxy-2'-methyl-[1,1'-biphenyl]-3-yl)methylene)amino)-2-fluorophenoxy)acetic acid (I-13)
2-(4-((3-(3,5-dimethylisoxazol-4-yl)benzyl)amino)-2-fluorophenoxy)acetic acid (I-14)
2-(4-((4'-propoxy-2'-methyl-[1,1'-biphenyl]-3-yl)methylene)amino)-2-fluorophenoxy)acetic acid (I-15)
2-(2-fluoro-4-(((2'-isopropyl-[1,1'-biphenyl]-3-methylene)amino)phenoxy)acetic acid (I-16)
2-(4-((4'-ethoxy-2',6'-dimethyl-[1,1'-biphenyl]-3-methylene)amino)phenoxy)acetic acid (I-17)
2-(4-((4'-methoxy-2',6'-dimethyl-[1,1'-biphenyl]-3-methylene)amino)phenoxy)acetic acid (I-18)
2-(4-(((4'-methoxy-2'-methyl-[1,1'-biphenyl]-3-yl)methylene)amino)-2-fluorophenoxy)acetic acid (I-19)
2-(4-((4'-methoxy-2',6'-dimethyl-[1,1'-biphenyl]-3-methylene)amino)-2-fluorophenoxy)acetic acid (I-20)
2-(4-((4'-methoxy-2'-methyl-[1,1'-biphenyl]-3-yl)methylene)amino)phenoxy)acetic acid (I-21)
2-(4-(((4'-isopropoxy-2'-methyl-[1,1'-biphenyl]-3-yl)methylene)amino)-2-fluorophenoxy)acetic acid (I-22)
2-(4-(((4'-isopropoxy-2'-methyl-[1,1'-biphenyl]-3-yl)methylene)amino)phenoxy)acetic acid (I-23)
2-(4-((2'-chloro-[1,1'-biphenyl]-3-methylene)amino)phenoxy)acetic acid (I-24)
2-(4-((2'-methyl-[1,1'-biphenyl]-3-methylene)amino)phenoxy)acetic acid (I-25)
2-(4-((2'-fluoro-[1,1'-biphenyl]-3-methylene)amino)phenoxy)acetic acid (I-26)
2-(4-((2'-chloro-4'-methyl-[1,1'-biphenyl]-3-methylene)amino)phenoxy)acetic acid (I-27)
2-(4-((2'-trifluoromethyl-[1,1'-biphenyl]-3-methylene)amino)phenoxy)acetic acid (I-28)
2-(4-((4'-trifluoromethoxy-2',6'-dimethyl-[1,1'-biphenyl]-3-methylene)amino)phenoxy)acetic acid (I-29)
2-(4-((4'-trifluoromethoxy-2'-methyl-[1,1'-biphenyl]-3-methylene)amino)phenoxy)acetic acid (I-30))
2-(4-(((4'-ethoxy-2'-methyl-[1,1'-biphenyl]-3-yl)methylene)amino)phenoxy)acetic acid (I-31)
2-(4-((2'-trifluoromethyl-[1,1'-biphenyl]-3-methylene)amino)phenoxy)acetic acid (I-32)
2-(4-((2'-trifluoromethoxy-[1,1'-biphenyl]-3-methylene)amino-2-fluoro)phenoxy)acetic acid (I-33)
2-(4-((4'-trifluoromethoxy-2',6'-dimethyl-[1,1'-biphenyl]-3-methylene)amino)-2-fluorophenoxy)acetic acid (I-34)
2-(4-((4'-trifluoromethoxy-2'-methyl-[1,1'-biphenyl]-3-methylene)amino)2-fluorophenoxy)acetic acid (I-35)
2-(2-fluoro-4-((4'-(2-ethoxyethoxy)-2',6'-dimethyl-[1,1'-biphenyl]-3-methylene)amino)phenoxy)acetic acid (I-36)
2-(4-((4'-(2-ethoxyethoxy)-2',6'-dimethyl-[1,1'-biphenyl]-3-methylene)amino)phenoxy)acetic acid (I-37)
2-(2-fluoro-4-((4'-(2-methoxymethoxy)-2',6'-dimethyl-[1,1'-biphenyl]-3-methylene)amino)phenoxy)acetic acid (I-38)
2-(4-((4'-(2-methoxymethoxy)-2',6'-dimethyl-[1,1'-biphenyl]-3-methylene)amino)phenoxy)acetic acid (I-39)
2-(2-fluoro-4-((4'-(2-ethoxymethoxy)-2',6'-dimethyl-[1,1'-biphenyl]-3-methylene)amino)phenoxy)acetic acid (I-40)
2-(4-((4'-(2-ethoxymethoxy)-2',6'-dimethyl-[1,1'-biphenyl]-3-methylene)amino)phenoxy)acetic acid (I-41)
2(2-fluoro-4-(((4'-(hexyloxy)-2',6'-dimethyl-[1,1'-biphenyl]-3-yl)methyl)amino)phenoxy)acetic acid (I-42)

2(4-(((4'-(hexyloxy)-2',6'-dimethyl-[1,1'-biphenyl]-3-yl)methyl)amino)phenoxy)acetic acid (I-43)
2(2-fluoro-4-(((4'-(cyclohexyloxy)-2',6'-dimethyl-[1,1'-biphenyl]-3-yl)methyl)amino)phenoxy)acetic acid (I-44)
2(4-(((4'-(cyclohexyloxy)-2',6'-dimethyl-[1,1'-biphenyl]-3-yl)methyl)amino)phenoxy)acetic acid (I-45).

Another aspect of the invention relates to a pharmaceutical composition comprising a therapeutically effective amount of a compound of formula (I), or a pharmaceutically acceptable salt thereof, and suitable carriers, diluents or excipients.

The invention also relates to the use of a compound of the formula (I), or a pharmaceutically acceptable salt thereof, or a pharmaceutical composition comprising a compound of the formula (I), in preparing a medicament for treating diabetes and metabolic syndrome.

DETAILED SUMMARY OF INVENTION

Unless otherwise stated, the following terms used in the description and claims have the following meanings.

"Alkyl" means a saturated aliphatic hydrocarbon group, including straight chain and branched groups of 1 to 20 carbon atoms. An alkyl group having 1 to 10 carbon atoms is preferred, an alkyl group having 1 to 6 carbon atoms is more preferred, an alkyl group having 1 to 3 carbon atoms is still more preferred, and methyl is most preferred. Non-limiting examples include methyl, ethyl, propyl, isopropyl, butyl, isobutyl, sec-butyl, tert-butyl, pentyl, isopentyl, neopentyl, hexyl, and the like, and various branched isomers and the like. The alkyl group may be substituted or unsubstituted, and when substituted, the substituent may substitute at any available point of attachment, and is preferably one or more of the following groups independently selected from the group consisting of halogen, hydroxy, cyano, nitro, alkyl, alkoxy, cycloalkyl, heterocyclic, aryl or heteroaryl group.

"Aryl" means a 6 to 14 membered all-carbon monocyclic or fused polycyclicgroup (ie, a ring that shares a pair of adjacent carbon atoms) having a conjugated π-electron system, preferably 6 to 10 membered, such as phenyl and naphthyl ring. The aryl ring may be fused to a heteroaryl, heterocyclyl or cycloalkyl ring wherein the ring to which the parent structure is attached is an aryl ring.

The aryl group may be substituted or unsubstituted, and when substituted, the substituent is preferably one or more of the following groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio group.

"Heteroaryl" refers to a heteroaromatic system containing 1 to 4 heteroatoms, 5 to 14 ring atoms, wherein the heteroatoms include O, S and N. 5 to 10-membered ring is preferred. The heteroaryl group is preferably 5- or 6-membered ring, such as furyl, thienyl, pyridyl, pyrrolyl, N-alkylpyrrolyl, pyrimidinyl, pyrazinyl, imidazolyl, tetrazolyl, isoxazolyl and the like. The heteroaryl ring may be fused to an aryl, heterocyclic or cycloalkyl ring wherein the ring to which the parent structure is attached is the heteroaryl ring.

"Alkoxy" means —O-(alkyl) and —O-(unsubstituted cycloalkyl), wherein alkyl is defined as above. Non-limiting examples include methoxy, ethoxy, propoxy, butoxy, cyclopropoxy, cyclobutoxy, cyclopentyloxy, cyclohexyloxy, and the like. The alkoxy group may be optionally substituted or unsubstituted, and when substituted, the substituent is preferably one or more of the following groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio group.

"Optional" or "optionally" means that the subsequently described event or environment may, but need not, occur, and the description includes the cases where the event or environment occurs or not. For example, "heterocyclic group optionally substituted by an alkyl group" means that an alkyl group may be, but not necessarily, present, and the description includes the case where the heterocyclic group is substituted with an alkyl group and the case where the heterocyclic group is not substituted with an alkyl group.

"Substituted" refers to one or more hydrogen atoms in the group, preferably at most 5, more preferably 1 to 3, hydrogen atoms are each independently substituted by a corresponding number of substituents. It goes without saying that the substituents are only in their possible chemical positions, and those skilled in the art will be able to determine (by experiment or theory) substitutions that may or may not be possible without too much effort. For example, an amino group or a hydroxyl group having a free hydrogen may be unstable when combined with a carbon atom having an unsaturated (e.g., olefinic) bond.

"Pharmaceutical composition" means a compound containing one or more of the compounds of the present invention, or a pharmaceutically acceptable salt thereof, or a mixture thereof, and other chemical components, such as pharmaceutically acceptable carriers and excipients. The purpose of the pharmaceutical composition is to promote the absorption of the active ingredient by the organism, and to facilitate the active ingredient to exert the biological activity in the living body.

The compounds of the formula (I) according to the invention can be synthesized by the following steps:

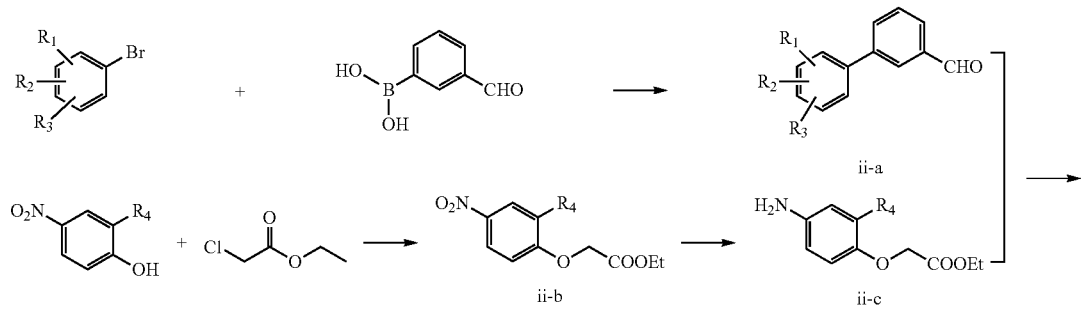

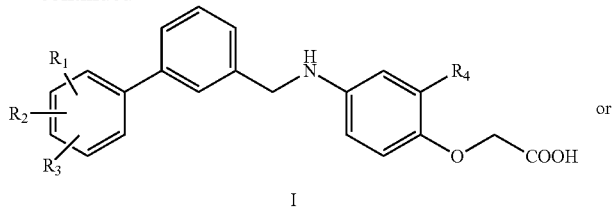

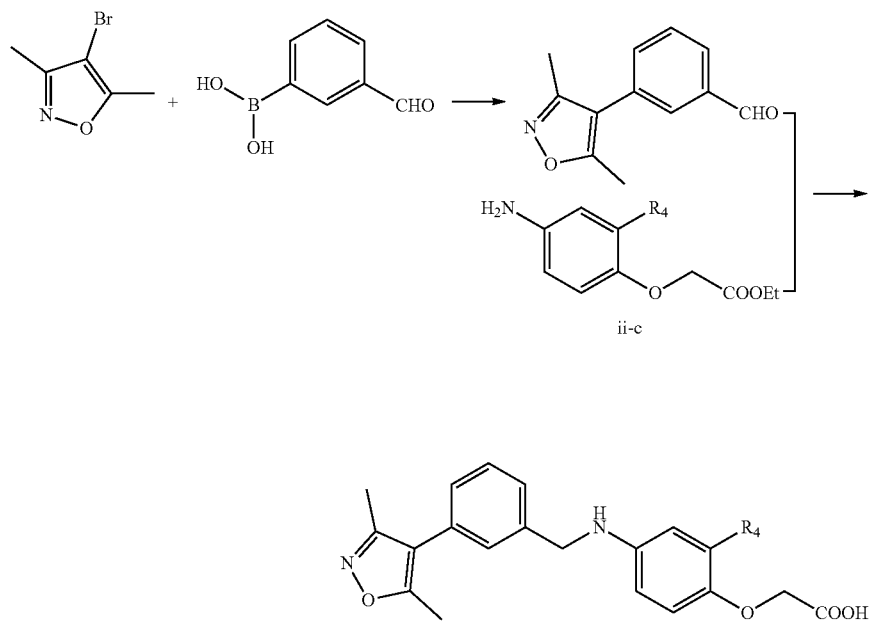

First, bromobenzene or 2,4-dimethyl-3-bromoisoxazole containing different substituents as a starting material is reacted with m-formylbenzeneboronic acid to form an intermediate ii-a. Ethyl chloroacetate and 2-fluoro-4-nitrophenol or p-nitrophenol react under basic conditions to form ii-b. ii-b is reduced to give an intermediate ii-c, and intermediates ii-a and ii-c react in the presence of a reducing agent to give compound I of the formula.

wherein: R 1 to $R_4$ are as defined in the formula (I).

The said base includes an inorganic base and an organic base, and the inorganic base may, for example, be an alkali metal carbonate such as sodium carbonate, potassium carbonate, cesium carbonate or the like; an alkali metal hydrogencarbonate such as potassium hydrogencarbonate or the like; an alkali metal hydroxide such as lithium hydroxide, sodium hydroxide, potassium hydroxide or the like; and the said organic base may, for example, be triethylamine, pyridine, dimethyl pyridine, n-butyllithium, potassium t-butoxide or the like.

The GPR40 agonistic activity and in vivo hypoglycemic activity of the compounds of the present invention can be determined by using an assay system as described below.

The following biological experimental examples are described to explain the present invention.

The experimental methods for the specific conditions in the experimental examples of the present invention are generally carried out under conventional conditions or in accordance with the conditions recommended by the commercial manufacturer. Reagents without specific source are commonly used reagents available in the market.

Experimental example 1 The agonistic activity of the compounds of the present invention on hGPR40-CHO stably transfected cells The present invention used the following method to determine the GPR40 agonistic activity of the compounds of the invention:

hGPR40-CHO stably transfected cells were seeded into a 96-well plate at a density of $3 \times 10^4$/well, and incubated overnight in a 37° C., 5% $CO_2$ cell incubator; the medium was discarded, 100 μl of HBSS was added to each well, and 100 μl of Fluo-4 dye solution containing Probenecid was added and incubated at 37° C. for 90 min. After the incubation, the Fluo-4 dye solution was sucked out, 100 μl of HBSS buffer was added, and the dye was washed away; 100 μl of HBSS containing Probenecid was added to each well, and incubated at 37° C. for 10 min; different concentrations of drugs were added to each well of the 96-well plate and FLIPR (Molecular Devices) was used for readings according to the parameter setting table. The experimental results were analyzed. Agonistic activity=(compound well fluorescence value−blank control well fluorescence value)/(linoleic acid well fluorescence value−blank control well fluorescence value)×100%, finally compounds with better agonistic activity were selected to determine their $EC_{50}$ at 100 nM, and the results are shown in Table 1.

TABLE 1 hGPR40 receptor agonistic activity

| Compound No. | Agonistic activity at 100 nM (%) | $EC_{50}(nM)^a$ | Compound No. | Agonistic activity at 100 nM (%) | EC50(nM) |
|---|---|---|---|---|---|
| I-1 | 79 | 24.2 ± 5.3 | I-23 | 62 | |
| I-2 | 84 | 16.3 ± 4.6 | I-24 | 80 | 18.6 ± 2.7 |
| I-3 | 87 | 4.8 ± 3.5 | I-25 | 82 | 17.3 ± 3.3 |
| I-4 | 65 | — | I-26 | 61 | |
| I-5 | 73 | — | I-27 | 69 | |
| I-6 | 53 | — | I-28 | 81 | 17.9 ± 2.9 |
| I-7 | 45 | — | I-29 | 62 | |
| I-8 | 86 | 11.7 ± 4.8 | I-30 | 76 | |
| I-9 | 67 | — | I-31 | 79 | |
| I-10 | 62 | — | I-32 | 46 | |
| I-11 | 46 | — | I-33 | 50 | |
| I-12 | 68 | — | I-34 | 64 | |
| I-13 | 85 | 14.6 ± 3.7- | I-35 | 78 | |
| I-14 | 54 | | I-36 | 56 | |
| I-15 | 75 | 28.4 ± 2.8 | I-37 | 50 | |
| I-16 | 63 | | I-38 | 64 | |
| I-17 | 70 | | I-39 | 60 | |
| I-18 | 65 | | I-40 | 63 | |
| I-19 | 80 | 18.4 ± 2.2 | I-41 | 59 | |
| I-20 | 68 | | | | |
| I-21 | 75 | | | | |
| I-22 | 65 | | TAK-875 | 65 | 37.1 ± 8.3 |

$^a EC_{50}$ values for GPR40 activities represent the mean of three determinations, results are expressed as mean ± SD,
— represents not test.

Conclusion: All compounds of the present invention have significant agonistic activity against GPR40, and most of the compounds have better activity than TAK-875.

Experimental example 2 In vivo hypoglycemic activity of the compounds of the present invention can be determined by using an assay system as described below:

Oral glucose tolerance test (OGTT) in normal mice: 10-week old clean Kunming mice (weighing 18-22 g, male), which were randomly divided into 7 groups, blank control group (bland solvent: 0.5% sodium carboxymethyl cellulose solution), positive drug control group (TAK-875: 20 mg/kg), test compound group (20 mg/kg), 8 mice in each group. The mice were fasted for 12 hours before experiment and water was taken freely, each group was administrated by gavage, blood was taken from the tail, and the blood glucose level was measured (recorded as −30 min). Then, the blank solvent, TAK-875 and the test compound were administered by gavage respectively, the blood glucose level was recorded as 0 min after 30 min, then a glucose solution having a concentration of 2 g/10 ml was administered by 10 ml/kg immediately, and blood glucose levels were determined at 15, 30, 60, and 120 min. The results are shown in Table 2.

TABLE 2

Effect of preferred compounds on oral glucose tolerance in normal mice ($\bar{x}$ ± SD, n = 8)

| Experimental group | −30 min | 0 min | 15 min | 30 min | 60 min | 120 min |
|---|---|---|---|---|---|---|
| Control | 4.27 ± 0.29 | 4.47 ± 0.47 | 14.38 ± 0.35 | 12.65 ± 0.47 | 8.53 ± 0.72 | 4.78 ± 0.65 |
| TAK-875 | 4.31 ± 0.26 | 4.53 ± 0.25 | 9.68 ± 0.46* | 8.61 ± 0.45* | 5.47 ± 0.56 | 4.46 ± 0.57 |
| I-2 | 4.18 ± 0.37 | 4.25 ± 0.38 | 6.24 ± 0.39* | 6.73 ± 0.29* | 4.28 ± 0.37 | 4.17 ± 0.52 |
| I-3 | 4.46 ± 0.52 | 4.61 ± 0.63 | 7.13 ± 0.29* | 6.94 ± 0.38* | 5.06 ± 0.23 | 4.38 ± 0.29 |
| I-8 | 4.34 ± 0.57 | 4.46 ± 0.47 | 6.73 ± 0.65* | 6.82 ± 0.58* | 5.17 ± 0.39 | 4.26 ± 0.25 |
| I-13 | 4.47 ± 0.38 | 4.61 ± 0.35 | 7.25 ± 0.58* | 7.03 ± 0.89* | 5.25 ± 0.72 | 4.38 ± 0.37 |
| I-19 | 4.34 ± 0.32 | 4.45 ± 0.56 | 9.08 ± 0.62 | 8.21 ± 0.39* | 5.23 ± 0.21 | 4.41 ± 0.44 |
| I-24 | 4.19 ± 0.28 | 4.39 ± 0.34 | 9.22 ± 0.57 | 8.04 ± 0.49* | 5.29 ± 0.34 | 4.33 ± 0.33 |
| I-25 | 4.23 ± 0.33 | 4.48 ± 0.39 | 8.47 ± 0.45 | 7.23 ± 0.39* | 5.11 ± 0.29 | 4.29 ± 0.39 |
| I-28 | 4.35 ± 0.36 | 4.56 ± 0.48 | 8.59 ± 0.38 | 7.43 ± 0.56* | 5.30 ± 0.26 | 4.21 ± 0.45 | note:
*$P \leq 0.05$ is the Student's t test result relative to the blank control group.

Oral glucose tolerance test in normal mice shows that compounds I-2, I-3, I-8, I-13, I-19, I-24, I-25 and I-28 can significantly improve oral glucose tolerance in mice, their hypoglycemic activity is even better than TAK-875 which is currently the only drug in phase III clinical trial, and therefore they have broad development prospects.

Experimental example 3 Evaluation of hepatotoxicity of the compounds of the present invention:

The test compounds were administered once a day for consecutive 4 weeks, blood was taken, and the contents of alanine aminotransferase (ALT), aspartate aminotransferase (AST), and total bilirubin (TBIL) were measured. The results are shown in Table 3.

TABLE 3

Effect of preferred compounds on serum AST, ALT and TBIL ($\bar{x} \pm SD$, n = 6).

| Group | ALT (IU/L) | AST (IU/L) | TBIL (IU/L) |
|---|---|---|---|
| STZ | 47.67 ± 4.8 | 118.33 ± 7.7 | 2.57 ± 0.3 |
| TAK-875 | 72.83 ± 8.4 | 149.33 ± 15.6 | 2.98 ± 0.4 |
| I-2 | 47 ± 5.3 | 118.43 ± 11.5 | 2.61 ± 0.5 |
| I-3 | 51.23 ± 5.6 | 103.27 ± 9.98 | 2.55 ± 0.4 |
| I-8 | 46.63 ± 6.2 | 112.85 ± 17.76 | 2.52 ± 0.3 |
| 1-13 | 52.37 ± 5.3 | 121.37 ± 13.2 | 2.48 ± 0.5 |
| I-19 | 50.33 ± 4.6 | 123.45 ± 7.8 | 2.68 ± 0.3 |
| I-24 | 52.68 ± 5.7 | 116.78 ± 12.4 | 2.56 ± 0.2 |
| I-25 | 51.78 ± 4.5 | 116.54 ± 8.9 | 2.69 ± 0.4 |
| I-28 | 49.36 ± 7.8 | 119.68 ± 7.3 | 2.57 ± 0.5 |

The results showed that in the positive drug TAK-875 group, AST was higher than STZ group, and there was a risk of hepatotoxicity, while AST, ALT and TBIL in compounds I-2, I-3, I-8 and I-13 were all equivalent to the blank group, indicating that the preferred compounds posed a very low risk of hepatotoxicity.

Experimental example 4 Primary hepatocyte bile acid reflux inhibition test of the compounds of the present invention:

Hepatocytes from male Sprague-Dawley rats were isolated by two-step collagenase digestion and inoculated into rat tail collagen I coated 24-well plates to establish a primary hepatocyte sandwich model. Before the start of the ingestion experiment, the cells were washed three times with warm standard HBSS buffer or $Ca^{2+}$-free HBSS buffer, and then 500 μl of standard HBSS buffer or $Ca^{2+}$-free HBSS buffer and 500 μl of the corresponding compound solution were added to each well, and the cells were incubated for 15 minutes. After the incubation, the cells were washed twice with warm HBSS or $Ca^{2+}$-free HBSS and incubate for 15 minutes at 37° C. in the same buffer. After removing the buffer, 250 μl of standard buffer was added to all wells, and 500 μl of the compound solution was added to the corresponding wells, and 250 μl of d8-TCA solution was added to each well to incubate the hepatocytes at 37° C. for 15 minutes.

After the incubation, the solution was sucked out of the cells, the cells were washed three times with ice-cold PBS to stop the ingestion, and the recovered rat hepatocytes were dissolved in 200 μl of deionized water through three freeze-thaw cycles, and the samples were stored at −20° C. for analysis. The protein concentration in the samples was analyzed by BCA, and the concentration of d8-TCA in hepatocytes was analyzed by liquid chromatography-tandem mass spectrometry (LC-MS/MS). The result (FIG. 1) showed that the compounds of the present invention had excellent hypoglycemic activity and a low risk of hepatotoxicity, and thus had broad development prospects. At the same time, selective experiments of GPR120 and PPARγ agonism on 1-3 compounds showed that the EC K was 54 μM and 83 μM, respectively, so the compound was a highly selective GPR40 agonist.

DESCRIPTION OF DRAWINGS

FIG. 1: d8-TCA concentration after administration of different compounds, wherein in each pair of data, the left contains $Ca^{2+}$ and the right does not contain $Ca^{2+}$.

EMBODIMENTS

The invention is further illustrated by the following examples. It should be noted that the following examples are for illustrative purposes only and are not intended to limit the invention. Various changes made by those skilled in the art in light of the teachings of the present invention are intended to be within the scope of the appended claims.

Example 1

(4-amino-2-fluorophenoxy) ethyl acetate

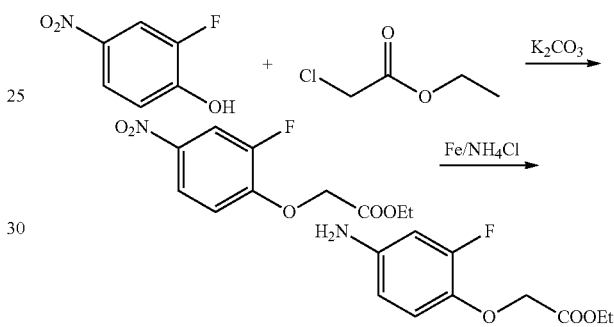

2-fluoro-4-nitrophenol (1 g, 6.37 mmol) was dissolved in 30 ml of acetonitrile, to which ethyl chloroacetate (0.94 g, 7.64 mmol) was added and stirred until it dissolved, and potassium carbonate (1.76 g, 12.73 mmol) was added. The mixture was heated to reflux for 3 hours, filtered under vacuum, and the filtrate was evaporated under reduced pressure to give 1.3 g of grey brown crude solid with yield of 83%.

The above crude solid (0.5 g, 2.6 mmol) was dissolved in 20 ml of 80% aqueous ethanol solution, iron powder (0.34 g, 6.17 mmol), ammonium chloride (0.55 g, 10.28 mmol) were added, and heated at 80° C. for 6 h. After the reaction was completed, the reaction solution was added with sodium carbonate to adjust the pH to 8-9, filtered with celite, and the filter cake was washed. The filtrate was concentrated under reduced pressure to give 0.3 g of dark brown crude solid with yield of 68.2%.

Example 2

2-(4-((4'-ethoxy-2',6'-dimethyl-[1,1'-biphenyl]-3-methylene)amino)-2-fluorophenoxy) acetic acid
(I-1)

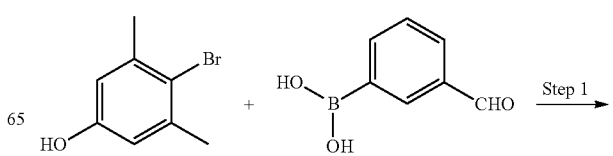

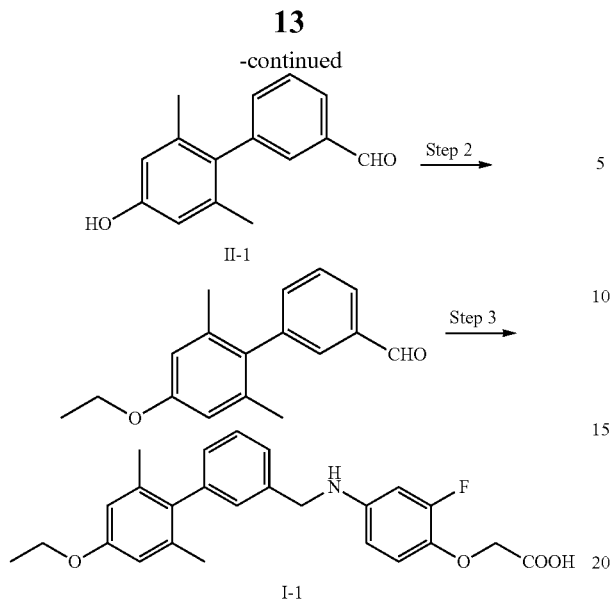

Step 1: 3,5-dimethyl-4-bromophenol (0.5 g, 2.49 mmol), m-formylbenzeneboronic acid (0.45 g, 2.98 mmol) were added to 42 ml of mixed solvent of toluene, ethanol and water (3:1:3), there mixture was stirred until it dissolved, sodium carbonate (0.5 g, 6.22 mmol), tetrakis(triphenylphosphine)palladium (0.02 g, 0.012 mmol) were added to react under $N_2$ atmosphere for 24 h at 80° C. After the reaction was completed, ethyl acetate (30 ml×4) was added as extraction agent, and the organic phases were combined and washed with saturated brine (20 ml×2), dried over anhydrous sodium sulfate and filtered, then the filtrate was evaporated under reduced pressure to give a brown oil which was purified by column chromatography (petroleum ether/ethyl acetate, 90:10, v/v) to give a white solid (II-1, 0.75 g, yield: 70%).

Step 2: II-1 (0.9 g, 2.21 mmol) was added to 20 ml of acetonitrile, stirred and dissolved, then ethyl bromide (0.29 g, 2.65 mmol) and potassium carbonate (0.46 g, 3.31 mmol) were added to react for 2 h at 65° C. After the reaction was completed, the filter cake obtained after vacuum filtering was washed with ethyl acetate and the filtrate was evaporated under reduced pressure to give a yellow solid (III-1, 0.45 g, yield: 80.3%).

Step 3: compound III-1 (0.3 g, 1.18 mmol) was dissolved in 20 ml of methanol, and (4-amino-2-fluorophenoxy) ethyl acetate (0.25 g, 1.18 mmo) was added and stirred at room temperature for 1 h. Sodium cyanoborohydride (0.11 g, 1.77 mmol) was added to react for 6 h. After completion of the reaction, the residue was purified by column chromatography (petroleum ether/ethyl acetate, 90:10, v/v) to give 0.4 g of pale yellow oily liquid. The obtained yellow oily liquid was dissolved in 4 mL of tetrahydrofuran, 6 mL of methanol and 2 mL of water and LiOH (0.2 g, 8 mmol) was added to react at room temperature for 4 h, the mixture was adjusted to pH 2-3 with 1N of dilute hydrochloric acid, and extracted with dichloromethane (30 ml×4), the organic phases were combined, washed with saturated brine (20 ml×2), dried over anhydrous sodium sulfate and filtered, the filtrate was evaporated under reduced pressure to give a brown oil which was purified by column chromatography (petroleum ether/ethyl acetate, 90:10, v/v) to give a white solid 2-(4-((4'-ethoxy-2',6'-dimethyl-[1,1'-biphenyl]-3-methylene)amino)-2-fluorophenoxy)acetic acid (0.2 g, m.p.: 102-104° C., yield: 40%).

$^1$H NMR (300 MHz, DMSO-$d_6$) δ: 7.43-7.26 (m, 2H), 7.04 (s, 1H), 6.95 (d, J=7.3 Hz, 1H), 6.81 (t, J=9.3 Hz, 1H), 6.65 (s, 2H), 6.42, 6.37 (dd, J=14.1, 2.5 Hz, 1H), 6.29 (d, J=8.9 Hz, 1H), 4.51 (s, 2H), 4.26 (s, 2H), 4.01 (q, J=7.0 Hz, 2H), 1.87 (s, 6H), 1.31 (t, J=7.0 Hz, 3H).

$^{13}$C NMR (75 MHz, DMSO-$d_6$) δ: 170.78, 157.55, 144.89, 140.61, 140.49, 136.93, 134.27, 128.87, 128.77, 128.07, 125.92, 117.63, 113.55, 108.23, 101.25, 66.90, 63.16, 47.14, 21.17, 15.23. ESI-MS m/z: 422.2 [M-H]$^-$. Anal. calcd. For $C_{25}H_{26}FNO_4$: C, 70.91; H, 6.19; N, 3.31; Found: C, 70.90; H, 6.17; N, 3.28.

Example 3

2-(4-((2'-chloro-[1,1'-biphenyl]-3-methylene)amino)-2-fluorophenoxy)acetic acid (I-2)

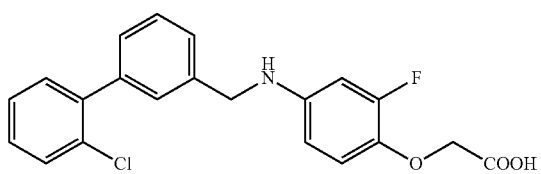

By substituting 2-chlorobromobenzene for the 3,5-dimethyl-4-bromophenol of Example 2, Compound I-2 was prepared in a similar manner as in Example 2 to give a white solid (0.42 g, m.p.: 134-135° C., yield: 69%).

$^1$H NMR (300 MHz, DMSO-$d_6$) δ: 12.91 (s, 1H), 7.61-7.23 (m, 8H), 6.84 (t, J=9.2 Hz, 1H), 6.47 (d, J=13.9 Hz, 1H), 6.33 (d, J=8.5 Hz, 1H), 4.52 (s, 2H), 4.28 (s, 2H). $^{13}$C NMR (75 MHz, DMSO-$d_6$) δ: 170.31, 154.21, 144.42, 140.01, 139.75, 138.60, 131.44, 131.23, 129.83, 129.13, 128.18, 127.55, 127.48, 126.63, 117.18, 107.55, 100.76, 100.47, 66.35, 46.68. ESI-MS m/z: 384.1 [M-H]$^-$. Anal. calcd. For $C_{21}H_{17}ClFNO_3$: C, 65.38; H, 4.44; N, 3.63; Found: C, 65.37; H, 4.45; N, 3.61.

Example 4

2-(4-((2'-methyl-[1,1'-biphenyl]-3-methylene)amino)-2-fluorophenoxy)acetic acid (I-3)

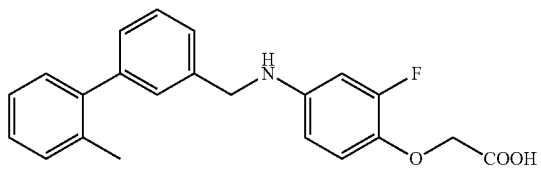 [SMILES: Cc1ccccc1-c1cccc(CNc2ccc(OCC(=O)O)c(F)c2)c1]

By substituting 2-methylbromobenzene for the 3,5-dimethyl-4-bromophenol of Example 2, Compound I-3 was prepared in a similar manner as in Example 2 to give a white solid, (0.51 g, m.p.: 103-104° C., yield: 85%).

$^1$H NMR (300 MHz, DMSO-$d_6$) δ: 7.42-7.14 (m, 8H), 6.82 (t, J=9.3 Hz, 1H), 6.47, 6.43 (dd, J=14.1, 2.5 Hz, 1H), 6.32 (d, J=8.8 Hz, 1H), 4.50 (s, 2H), 4.27 (s, 2H), 2.17 (s, 3H). $^{13}$C NMR (75 MHz, DMSO-$d_6$) δ: 170.80, 154.74, 151.54, 144.81, 141.71, 140.36, 136.59, 135.12, 130.79, 129.88, 128.69, 128.37, 127.70, 126.36, 126.30, 117.71, 108.04, 101.26, 66.96, 47.18, 20.54. ESI-MS m/z: 364.1

[M-H]⁻. Anal. calcd. For $C_{22}H_{20}FNO_3$: C, 72.31; H, 5.52; N, 3.83; Found: C, 72.32; H, 5.54; N, 3.82.

Example 5

2-(4-((2'-fluoro-[1,1'-biphenyl]-3-methylene)amino)-2-fluorophenoxy)acetic acid (I-4)

By substituting 2-fluorobromobenzene for the 3,5-dimethyl-4-bromophenol of Example 2, Compound I-4 was prepared in a similar manner as in Example 2 to give a pale yellow solid (0.46 g, m.p.: 105-107° C., yield: 76%).

$^1$H NMR (300 MHz, DMSO-d$_6$) δ: 7.53-7.28 (m, 8H), 6.83 (t, J=9.3 Hz, 1H), 6.48, 6.44 (dd, J=14.1, 2.5 Hz, 1H), 6.32 (d, J=7.0 Hz, 1H), 4.53 (s, 2H), 4.28 (s, 2H). $^{13}$C NMR (75 MHz, DMSO-d$_6$) δ: 170.29, 160.64, 154.23, 151.04, 144.44, 140.41, 135.05, 130.75, 129.56, 128.54, 127.71, 126.76, 124.91, 117.23, 116.22, 115.92, 107.48, 100.73, 66.39, 46.74. ESI-MS m/z: 368.1 [M-H]⁻. Anal. calcd. For $C_{21}H_{17}FNO_3$: C, 68.29; H, 4.64; N, 3.79; Found: C, 68.28; H, 4.66; N, 3.77.

Example 6

2-(4-((2'-chloro-4'-methyl-[1,1'-biphenyl]-3-methylene)amino)-2-fluorophenoxy)acetic acid (I-5)

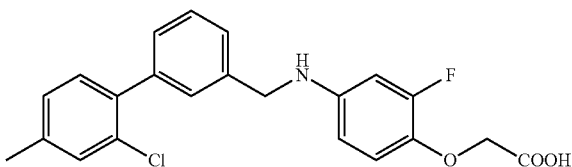 [SMILES: Cc1ccc(-c2cccc(CNc3ccc(OCC(=O)O)c(F)c3)c2)c(Cl)c1]

By substituting 2-chloro-4-methylbromobenzene for the 3,5-dimethyl-4-bromophenol of Example 2, Compound I-5 was prepared in a similar manner as in Example 2 to give a pale white solid (0.42 g, m.p.: 141-143° C., yield: 72%).

$^1$H NMR (300 MHz, DMSO-d$_6$) δ: 7.50-7.17 (m, 7H), 6.96 (t, J=9.3 Hz, 1H), 6.48, 6.44 (dd, J=14.2, 2.6 Hz, 1H), 6.32 (d, J=7.1 Hz, 1H), 4.62 (s, 2H), 4.37 (s, 2H), 2.35 (s, 3H). $^{13}$C NMR (75 MHz, DMSO-d$_6$) δ: 170.20, 154.08, 150.88, 138.97, 138.59, 136.73, 131.13, 130.06, 128.44, 128.14, 127.76, 126.69, 117.03, 108.61, 101.67, 66.29, 47.30, 20.22. ESI-MS m/z: 398.1 [M-H]⁻. Anal. calcd. For $C_{22}H_{19}ClFNO_3$: C, 66.09; H, 4.79; N, 3.50; Found: C, 66.07; H, 4.76; N, 3.53.

Example 7

2-(4-((2'-methoxy-[1,1'-biphenyl]-3-methylene)amino)-2-fluorophenoxy)acetic acid (I-6)

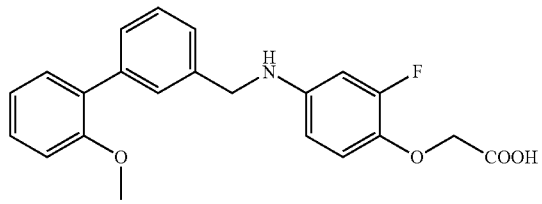 [SMILES: COc1ccccc1-c1cccc(CNc2ccc(OCC(=O)O)c(F)c2)c1]

By substituting 2-bromophenol for the 3,5-dimethyl-4-bromophenol in Example 2 and substituting methyl iodide for ethyl bromide in Example 2, Compound I-6 was prepared in the same manner as in Example 2 to give an off-white solid (0.52 g, m.p. 95-96° C., yield 82%).

$^1$H NMR (300 MHz, DMSO-ds) δ: 7.44 (s, 1H), 7.35-7.24 (m, 5H), 7.09 (d, J=8.1 Hz, 1H), 7.02 (t, J=7.3 Hz, 1H), 6.83 (t, J=9.3 Hz, 1H), 6.48, 6.44 (dd, J=14.1, 2.6 Hz, 1H), 6.32 (d, J=8.7 Hz, 1H), 4.52 (s, 2H), 4.24 (s, 2H), 3.72 (s, 3H). $^{13}$C NMR (75 MHz, DMSO-d$_6$) δ: 170.82, 156.50, 151.51, 144.97, 140.09, 138.59, 136.54, 130.79, 130.24, 129.30, 128.65, 128.36, 126.25, 121.18, 117.64, 112.12, 107.97, 101.18, 66.87, 55.82, 47.29. ESI-MS m/z: 381.1 [M-H]⁻. Anal. calcd. For $C_{22}H_{19}ClFNO_3$: C, 69.28; H, 5.29; N, 3.67; Found: C, 69.27; H, 5.28; N, 3.65.

Example 8

2-(4-((2'-Nitrile-[1,1'-biphenyl]-3-methylene)amino)-2-fluorophenoxy)acetic acid (I-7)

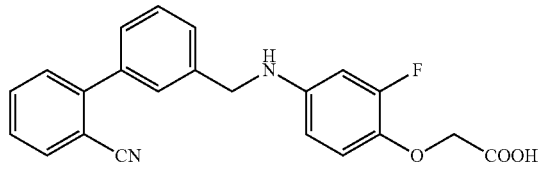 [SMILES: N#Cc1ccccc1-c1cccc(CNc2ccc(OCC(=O)O)c(F)c2)c1]

By substituting 2-carbonitrile-bromobenzene for the 3,5-dimethyl-4-bromophenol of Example 2, Compound I-7 was prepared in a similar manner as in Example 2 to give an off-white solid (0.43 g, m.p. 137-140° C., yield 76%).

$^1$H NMR (300 MHz, DMSO-ds) δ: 7.96 (d, J=7.3 Hz, 1H), 7.80 (t, J=7.1 Hz, 1H), 7.66-7.54 (m, 3H), 7.50-7.46 (m, 3H), 6.82 (t, J=9.3 Hz, 1H), 6.49, 6.45 (dd, J=14.0, 2.4 Hz, 1H), 6.32 (d, J=8.7 Hz, 1H), 4.52 (s, 2H), 4.30 (s, 2H). $^{13}$C NMR (75 MHz, DMSO-d$_6$) δ: 170.32, 152.93, 144.52, 140.74, 137.80, 136.23, 133.84, 133.51, 130.05, 128.68, 128.18, 127.65, 127.53, 127.08, 118.52, 117.18, 107.42, 66.43, 46.72. ESI-MS m/z: 375.1 [M-H]⁻. Anal. calcd. For $C_{22}H_{17}FN_2O_3$: C, 70.20; H, 4.55; N, 7.44; Found: C, 70.21; H, 4.53; N, 7.46.

Example 9

2-(4-((2'-trifluoromethyl-[1,1'-biphenyl]-3-methylene)amino)-2-fluorophenoxy)acetic acid (I-8)

By substituting 2-trifluoromethylbromobenzene for the 3,5-dimethyl-4-bromophenol of Example 2, Compound I-8 was prepared in a similar manner as in Example 2 to give a white solid (0.34 g, m.p. 120° C., yield 61%).

$^1$H NMR (300 MHz, DMSO-$d_6$) δ: 12.83 (brs, 1H), 7.83 (d, J=7.7 Hz, 1H), 7.72 (t, J=7.4 Hz, 1H), 7.61 (t, J=7.6 Hz, 1H), 7.45-7.36 (m, 3H), 7.29 (s, 1H), 7.21-7.17 (m, 1H), 6.82 (t, J=9.3 Hz, 1H), 6.45, 6.41 (dd, J=14.1, 2.6 Hz, 1H), 6.30 (d, J=8.9 Hz, 1H), 4.52 (s, 2H), 4.26 (s, 2H). $^{13}$C NMR (75 MHz, DMSO-$d_6$) δ: 170.31, 154.23, 151.03, 144.44, 140.71, 139.75, 136.12, 135.97, 132.19, 127.95, 127.00, 126.55, 126.02, 125.95, 122.30, 117.19, 107.56, 100.69, 66.41, 46.69. ESI-MS m/z: 418.1 [M-H]$^-$. Anal. calcd. For $C_{22}H_{17}F_4NO_3$: C, 63.01; H, 4.09; N, 3.34; Found: C, 63.03; H, 4.07; N, 3.36.

Example 10

2-(4-((4'-propoxy-2',6'-dimethyl-[1,1'-biphenyl]-3-methylene)amino)-2-fluorophenoxy) acetic acid (I-9)

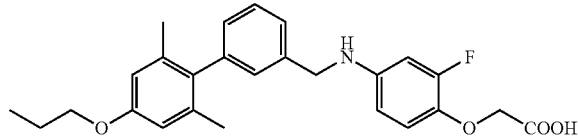 [SMILES: CCCOc1cc(C)c(-c2cccc(CNc3ccc(OCC(=O)O)c(F)c3)c2)c(C)c1]

By substituting 1-bromopropane for bromoethane of Example 2, Compound I-9 was prepared in a similar manner as in Example 2 to give a off-white solid (0.41 g, m.p. 95-96° C., yield 71%).

$^1$H NMR (300 MHz, DMSO-$d_6$) δ: 12.98 (brs, 1H), 7.45-7.25 (m, 2H), 7.06 (s, 1H), 6.96 (d, J=7.3 Hz, 1H), 6.84 (t, J=9.2 Hz, 1H), 6.66 (s, 2H), 6.48 (d, J=14.6 Hz, 1H), 6.36 (d, J=8.4 Hz, 1H), 4.54 (s, 2H), 4.29 (s, 2H), 3.91 (t, J=6.5 Hz, 2H), 1.87 (s, 6H), 1.75-1.68 (m, 2H), 0.98 (t, J=7.4 Hz, 3H). $^{13}$C NMR (75 MHz, DMSO-$d_6$) δ: 170.66, 157.74, 152.34, 140.67, 139.67, 136.94, 134.21, 129.08, 128.89, 128.29, 126.22, 117.53, 113.59, 107.56, 69.15, 66.81, 55.35, 22.58, 21.13, 10.89. ESI-MS m/z: 436.2 [M-H]$^-$. Anal. calcd. For $C_{26}H_{28}FNO_4$: C, 71.38; H, 6.45; N, 3.20; Found: C, 71.37; H, 6.43; N, 3.22.

Example 11

2-(2-fluoro-4-((4'-(2-methoxyethoxy)-2',6'-dimethyl-[1,1'-biphenyl]-3-methylene)amino phenoxy)acetic acid (I-10)

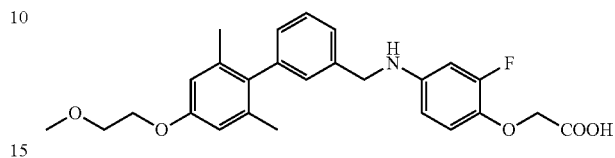

By substituting bromoethanol for bromoethane in Example 2, Compound I-10 was prepared in the same manner as in Example 2 to give a white solid (0.52 g, m.p. 138-140° C., yield: 82%).

$^1$H NMR (300 MHz, DMSO-$d_6$) δ: 12.85 (brs, 1H), 7.38-7.29 (m, 2H), 7.05 (s, 1H), 6.96 (d, J=6.9 Hz, 1H), 6.82 (t, J=9.2 Hz, 1H), 6.68 (s, 2H), 6.40 (d, J=14.1 Hz, 1H), 6.29 (d, J=8.1 Hz, 1H), 4.52 (s, 2H), 4.27 (s, 2H), 4.07 (t, J=3.4 Hz, 2H), 3.64 (t, J=3.4 Hz, 2H), 3.32 (s, 3H), 1.88 (s, 6H). $^{13}$C NMR (75 MHz, DMSO-$d_6$) δ: 170.28, 157.01, 140.08, 139.97, 136.51, 133.98, 128.40, 128.28, 127.58, 125.48, 117.15, 113.11, 107.80, 100.84, 70.40, 66.60, 66.39, 58.11, 46.69, 20.66. ESI-MS m/z: 455.2 [M-H]$^-$. Anal. calcd. For $C_{26}H_{28}FNO_5$: C, 68.86; H, 6.22; N, 3.09; Found: C, 68.85; H, 6.24; N, 3.06.

Example 12

2-(4-((([1,1'-biphenyl]-3-methylene)amino)-2-fluorophenoxy)acetic acid (I-11)

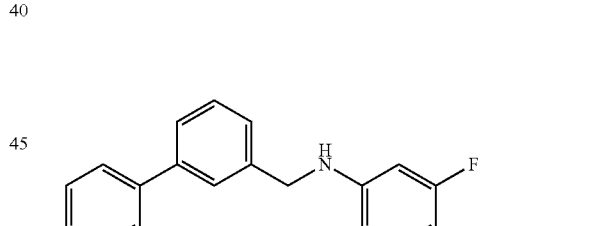

By substituting bromobenzene for the 3,5-dimethyl-4-bromophenol of Example 2, Compound I-11 was prepared in a similar manner as in Example 2 to give a white solid (0.23 g, m.p. 115-116° C., yield 41%).

$^1$H NMR (300 MHz, DMSO-$d_6$) δ: 7.69-7.59 (m, 3H), 7.55-7.30 (m, 6H), 6.83 (t, J=9.3 Hz, 1H), 6.50, 6.45 (dd, J=14.1, 2.6 Hz, 1H), 6.34, 6.31 (dd, J=8.8, 1.5 Hz, 1H), 4.53 (s, 2H), 4.28 (s, 2H). $^{13}$C NMR (75 MHz, DMSO-$d_6$) δ: 170.32, 154.24, 151.05, 144.47, 140.68, 140.18, 136.16, 128.89, 127.40, 126.65, 126.37, 125.67, 125.09, 117.21, 107.52, 100.79, 66.43, 46.86. ESI-MS m/z: 350.1 [M-H]$^-$. Anal. calcd. For $C_2H_{18}FNO_3$: C, 71.78; H, 5.16; N, 3.99; Found: C, 71.77; H, 5.14; N, 3.97.

Example 13

2-(4-(((2',6'-dimethyl-4'-(3-(methylsulfonyl)propoxy)-[1,1'-biphenyl]-3-methylene)amino)-2-fluorophenoxy)acetic acid (I-12)

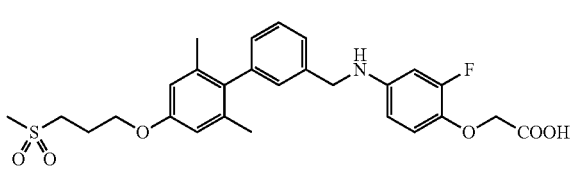 [SMILES: Cc1cc(OCCCS(C)(=O)=O)cc(C)c1-c1cccc(CNc2ccc(OCC(=O)O)c(F)c2)c1]

By substituting 1-bromo-3-(methylsulfonyl)propane for ethyl bromide of Example 2, Compound I-12 was prepared in a similar manner as in Example 2 to give an off-white solid (0.26 g, m.p. 69-70° C., yield 38%).

$^1$H NMR (300 MHz, DMSO-d$_6$) δ: 7.45-7.24 (m, 2H), 7.05 (s, 1H), 6.96 (d, J=7.2 Hz, 1H), 6.80 (t, J=9.4 Hz, 1H), 6.69 (s, 2H), 6.43, 6.38 (dd, J=14.1, 2.4 Hz, 1H), 6.29 (d, J=8.7 Hz, 1H), 4.52 (s, 2H), 4.26 (s, 2H), 4.08 (t, J=6.0 Hz, 2H), 3.27 (t, J=6.6 Hz, 2H), 3.03 (s, 3H), 2.21-2.06 (m, 2H), 1.88 (s, 6H). $^{13}$C NMR (75 MHz, DMSO-d$_6$) δ: 170.30, 156.82, 154.19, 151.01, 144.28, 140.04, 136.57, 134.17, 128.41, 128.25, 127.54, 125.49, 117.16, 113.20, 107.76, 100.78, 66.43, 65.33, 50.51, 46.65, 22.01, 20.65. ESI-MS m/z: 514.2 [M-H]$^-$. Anal. calcd. For C$_{27}$H$_{30}$FNO$_6$S: C, 62.90; H, 5.87; N, 2.72; Found: C, 62.92; H, 5.85; N, 2.75.

Example 14

2-(4-(((4'-ethoxy-2'-methyl-[1,1'-biphenyl]-3-yl)methylene)amino)-2-fluorophenoxy)acetic acid (I-13)

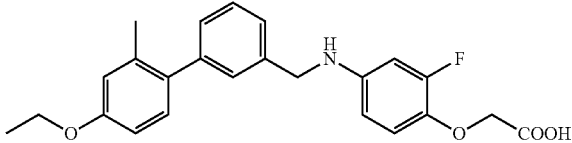 [SMILES: CCOc1ccc(-c2cccc(CNc3ccc(OCC(=O)O)c(F)c3)c2)c(C)c1]

By substituting 3-methyl-4-bromophenol for 3,5-dimethyl-4-bromophenol in Example 2, Compound I-13 was prepared in a similar manner as in Example 2 to give a white solid (0.32 g, m.p. 95-96° C., yield 63%).

$^1$H NMR (300 MHz, DMSO-d$_6$) δ: 12.89 (s, 1H), 7.47-7.23 (m, 3H), 7.15 (d, J=7.4 Hz, 1H), 7.08 (d, J=8.3 Hz, 1H), 6.97-6.66 (m, 3H), 6.46 (dd, J=14.0, 2.5 Hz, 1H), 6.32 (d, J=8.0 Hz, 1H), 4.52 (s, 2H), 4.26 (s, 2H), 4.04 (q, J=7.0 Hz, 2H), 2.15 (s, 3H), 1.33 (t, J=6.9 Hz, 3H). $^{13}$C NMR (75 MHz, DMSO-d$_6$): 170.32, 157.60, 144.47, 144.34, 140.92, 139.76, 136.02, 135.91, 133.60, 130.49, 128.11, 127.39, 125.43, 117.18, 114.50, 111.78, 107.55, 66.38, 62.85, 46.69, 20.35, 14.67. ESI-MS m/z: 408.2 [M-H]$^-$. Anal. calcd. For C$_{24}$H$_{24}$FNO$_4$: C, 70.40; H, 5.91; N, 3.42; Found: C, 70.43; H, 5.92; N, 3.43.

Example 15

2-(4-((3-(3,5-dimethylisoxazol-4-yl)benzyl)amino)-2-fluorophenoxy)acetic acid (I-14)

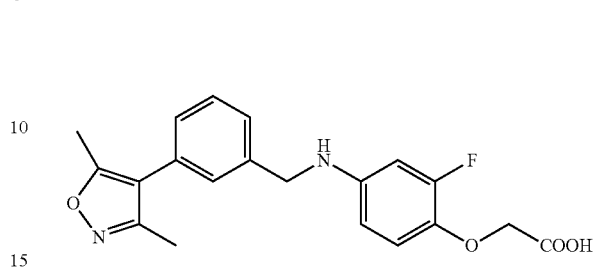

By substituting 4-bromo-3,5-dimethylisoxazole for 3,5-dimethyl-4-bromophenol in Example 2, Compound I-14 was prepared in a similar manner as in Example 2 to give a glassy light yellow solid (0.21 g, m.p. 72-73° C., yield 34%).

$^1$H NMR (300 MHz, DMSO-d$_6$) δ: 12.86 (brs, 1H), 7.49-7.14 (m, 4H), 6.83 (t, J=93 Hz, 1H), 6.47 (d, J=13.8 Hz, 1H), 6.32 (d, J=8.6 Hz, 1H), 4.53 (s, 2H), 4.27 (s, 2H), 2.35 (s, 3H), 2.17 (s, 3H). $^{13}$C NMR (75 MHz, DMSO-d$_6$) δ: 170.76, 165.48, 158.52, 144.83, 143.66, 141.13, 130.16, 129.30, 128.16, 127.64, 127.29, 126.91, 117.78, 108.16, 101.29, 63.16, 46.93, 11.68, 10.84. ESI-MS m/z: 369.1 [M-H]$^-$. Anal. calcd. For C$_{20}$H$_{19}$FN$_2$O$_4$: C, 64.86; H, 5.17; N, 7.56; Found: C, 64.84; H, 5.16; N, 7.53.

Example 16

2-(4-(((4'-propoxy-2'-methyl-[1,1'-biphenyl]-3-yl)methylene)amino)-2-fluorophenoxy) acetic acid (I-15)

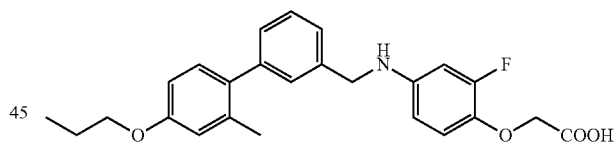

By substituting 3-methyl-4-bromophenol for the 3,5-dimethyl-4-bromophenol in Example 2 and substituting 1-bromopropane for the ethyl bromide in Example 2, Compound I-15 was prepared in a similar manner as in Example 2 to give a white solid (0.25 g, m.p. 75-76° C., yield 36%).

$^1$H NMR (300 MHz, DMSO-d$_6$) δ: 12.98 (brs, 1H), 7.41-7.23 (m, 3H), 7.15 (d, J=7.2 Hz, 1H), 7.08 (d, J=8.3 Hz, 1H), 6.91-6.74 (m, 3H), 6.48, 6.43 (dd, J=14.1, 2.1 Hz, 1H), 6.32 (d, J=8.6 Hz, 1H), 4.53 (s, 2H), 4.26 (s, 2H), 3.93 (t, J=6.5 Hz, 2H), 2.15 (s, 3H), 1.81-1.62 (m, 2H), 0.98 (t, J=7.4 Hz, 3H). $^{13}$C NMR (75 MHz, DMSO-ds) δ: 170.33, 157.77, 144.49, 140.95, 139.75, 136.09, 135.94, 133.61, 130.49, 128.11, 127.39, 125.42, 117.22, 116.19, 111.79, 107.55, 100.75, 68.80, 66.44, 46.72, 22.05, 20.32, 10.37. ESI-MS m/z: 422.2 [M-H]$^-$. Anal. calcd. For C$_{25}$H$_{26}$FNO$_4$: C, 70.91; H, 6.19; N, 3.31; Found: C, 70.93; H, 6.17; N, 3.33.

Example 17

2-(2-fluoro-4-(((2'-isopropyl-[1,1'-biphenyl]-3-methylene)amino)phenoxy)acetic acid (I-16)

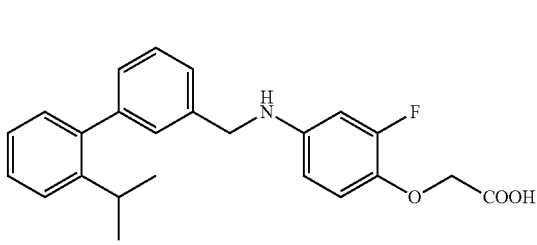 [SMILES: CC(C)c1ccccc1-c1cccc(CNc2ccc(OCC(=O)O)c(F)c2)c1]

By substituting 2-isopropylbromobenzene for the 3,5-dimethyl-4-bromophenol of Example 2, Compound I-16 was prepared in a similar manner as in Example 2 to give a white solid (0.28 g, m.p. 137-140° C., yield 56%).

$^1$H NMR (300 MHz, DMSO-d$_6$) δ: 7.46-7.28 (m, 4H), 7.21 (m, 2H), 7.11 (m, 2H), 6.83 (t, J=9. 137-140° C. 3 Hz, 1H), 6.45, 6.40 (dd, J=14.1, 2.3 Hz, 1H), 6.31 (d, J=8.6 Hz, 1H), 4.52 (s, 2H), 4.28 (s, 2H), 2.95-2.86 (m, 1H), 1.04 (d, J=6.8 Hz, 6H). $^{13}$C NMR (75 MHz, DMSO-d6) δ: 170.77, 154.76, 151.57, 146.16, 144.91, 141.78, 140.96, 140.29, 136.57, 129.92, 128.68, 128.25, 127.70, 126.23, 125.93, 117.74, 108.04, 101.19, 66.98, 47.09, 29.27, 24.43. ESI-MS m/z: 392.2 [M-H]$^-$. Anal. calcd. For C$_{24}$H$_{24}$FNO$_3$: C, 73.26; H, 6.15; N, 3.56; Found: C, 73.25; H, 6.14; N, 3.54.

Example 18

2-(4-((4'-ethoxy-2',6'-dimethyl-[1,1'-biphenyl]-3-methylene)amino)phenoxy)acetic acid (I-17)

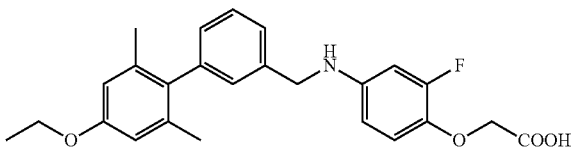 [SMILES: CCOc1cc(C)c(-c2cccc(CNc3ccc(OCC(=O)O)c(F)c3)c2)c(C)c1]

By substituting 4-nitrophenol for the 2-fluoro-4-nitrophenol in Example 1, Compound I-17 was prepared in a similar manner as in Example 2 to give a white solid (0.31 g, m.p. 135-138° C., yield 56%).

$^1$H NMR (300 MHz, DMSO-d$_6$) δ: 7.43-7.29 (m, 2H), 7.08 (s, 1H), 6.98 (d, J=6.6 Hz, 1H), 6.73 (s, 4H), 6.65 (s, 2H), 4.52 (s, 2H), 4.33 (s, 2H), 4.00 (q, J=6.9 Hz, 2H), 1.86 (s, 6H), 1.32 (t, J=13.1 Hz, 3H). $^{13}$C NMR (75 MHz, DMSO-d$_6$) δ: 170.37, 157.10, 146.51, 142.13, 140.18, 136.48, 133.64, 129.27, 128.35, 128.14, 126.36, 115.24, 113.04, 65.06, 62.67, 20.70, 14.72. ESI-MS m/z: 404.2 [M-H]$^-$. Anal. calcd. For C$_{25}$H$_{27}$NO$_4$: C, 74.05; H, 6.71; N, 3.45; Found: C, 74.04; H, 6.74; N, 3.42.

Example 19

2-(4-((4'-methoxy-2',6'-dimethyl-[1,1'-biphenyl]-3-methylene)amino)phenoxy)acetic acid (I-18)

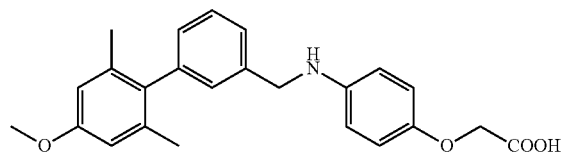 [SMILES: COc1cc(C)c(-c2cccc(CNc3ccc(OCC(=O)O)cc3)c2)c(C)c1]

By substituting 4-nitrophenol for the 2-fluoro-4-nitrophenol in Example 1 and substituting methyl iodide for the ethyl bromide in Example 2, Compound I-18 was prepared in a similar manner as in Example 2 to give a white solid (0.46 g, m.p. 131-134° C., yield 53%).

$^1$H NMR (300 MHz, DMSO-d$_6$) δ: 7.43-7.29 (m, 2H), 7.08 (s, 1H), 6.98 (d, J=6.6 Hz, 1H), 6.73 (s, 4H), 6.65 (s, 2H), 4.57 (s, 2H), 4.32 (s, 2H), 3.89 (s, 3H), 1.86 (s, 6H). $^{13}$C NMR (75 MHz, DMSO-d$_6$) δ: 170.37, 157.10, 146.51, 142.13, 140.18, 136.48, 133.64, 129.27, 128.35, 128.14, 126.36, 115.24, 113.04, 65.06, 55.9, 20.70. ESI-MS m/z: 391.18 [M-H]$^-$. Anal. calcd. For C$_{24}$H$_{25}$NO$_4$: C, 73.64; H, 6.44; N, 3.58; Found: C, 73.65; H, 6.46; N, 3.57.

Example 20

2-(4-(((4'-methoxy-2'-methyl-[1,1'-biphenyl]-3-yl)methylene)amino)-2-fluorophenoxy) acetic acid (I-19)

By substituting 3-methyl-4-bromophenol for the 3,5-dimethyl-4-bromophenol in Example 2 and substituting methyl iodide for the ethyl bromide in Example 2, Compound I-19 was prepared in a similar manner as in Example 2 to give a white solid (0.26 g, m.p. 129-132° C., yield of 63%).

$^1$H NMR (300 MHz, DMSO-d$_6$) δ: 7.43-7.29 (m, 3H), 7.08 (s, 1H), 6.98 (d, J=6.6 Hz, 1H), 6.73 (s, 4H), 6.65 (s, 2H), 4.57 (s, 2H), 4.32 (s, 2H), 3.70 (s, 3H), 2.27 (s, 3H). $^{13}$C NMR (75 MHz, DMSO-d$_6$) δ: 169.9, 159.4, 152.9, 142.1, 141.5, 137.9, 136.3, 133.6, 128.8, 125.9, 116.7, 113.6, 111.6, 103.0, 67.5, 55.8, 48.3, 19.0. ESI-MS m/z: 395.16 [M-H]$^-$. Anal. calcd. For C$_{23}$H$_{22}$NO$_4$: C, 69.86; H, 5.61; N, 3.54; Found: C, 69.87; H, 5.62; N, 3.53.

Example 21

2-(4-((4'-methoxy-2',6'-dimethyl-[1,1'-biphenyl]-3-methylene)amino)-2-fluorophenoxy)acetic acid (I-20)

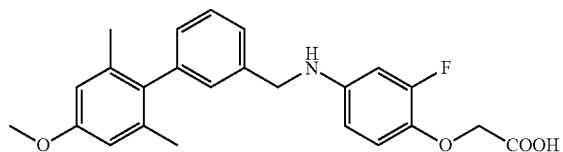 [SMILES: COc1cc(C)c(-c2cccc(CNc3ccc(OCC(=O)O)c(F)c3)c2)c(C)c1]

By substituting methyl iodide for the ethyl bromide in Example 2, Compound I-20 was prepared in a similar manner as in Example 2 to give a white solid (0.36 g, m.p. 133-136° C., yield 64%).

$^1$H NMR (300 MHz, DMSO-ds) δ: 7.57-7.41 (m, 4H), 6.94 (d, J=6.6 Hz, 2H), 6.77 (s, 1H), 6.54 (s, 2H), 4.66 (s, 2H), 4.32 (s, 2H), 3.81 (s, 3H), 2.57 (s, 6H). $^{13}$C NMR (75 MHz, DMSO-d$_6$) δ: 169.9, 159.3, 152.9, 142.1, 141.5, 138.2, 137.9, 136.3, 130.9, 129.0, 128.7, 125.8, 116.7, 111.4, 110.6, 103.0, 67.5, 55.8, 48.3, 19.3. ESI-MS m/z: 409.17 [M-H]$^-$. Anal. calcd. For C$_{24}$H$_{24}$NO$_4$: C, 70.40; H, 5.91; N, 3.42; Found: C, 70.41; H, 5.92; N, 3.42.

Example 22

2-(4-(((4'-methoxy-2'-methyl-[1,1'-biphenyl]-3-yl)methylene)amino)phenoxy)acetic acid (I-21)

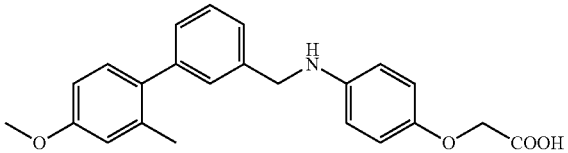 [SMILES: COc1ccc(-c2cccc(CNc3ccc(OCC(=O)O)cc3)c2)c(C)c1]

By substituting 4-nitrophenol for the 2-fluoro-4-nitrophenol in Example 1, substituting 3-methyl-4-bromophenol for the 3,5-dimethyl-4-bromophenol in Example 2, and substituting methyl iodide for the ethyl bromide in Example 2, Compound I-21 was prepared in a similar manner as in Example 2 to give a white solid (0.41 g, m.p. 121-124° C., yield 51%).

$^1$H NMR (300 MHz, DMSO-d$_6$) δ: 7.43-7.29 (m, 3H), 7.08 (s, 1H), 6.98 (d, J=6.6 Hz, 1H), 6.73 (s, 4H), 6.65 (s, 2H), 4.57 (s, 2H), 4.32 (s, 2H), 3.70 (s, 3H), 2.27 (s, 3H). $^{13}$C NMR (75 MHz, DMSO-d$_6$) δ: 169.9, 159.4, 146.5, 142.1, 141.6, 136.3, 133.6, 129.0, 128.8, 128.14, 125.8, 115.1, 113.6, 64.7, 55.8, 19.70. ESI-MS m/z: 377.16 [M-H]$^-$. Anal. calcd. For C$_{23}$H$_{23}$NO$_4$: C, 73.19; H, 6.14; N, 3.71; Found: C, 73.18; H, 6.14; N, 3.72.

Example 23

2-(4-(((4'-isopropoxy-2'-methyl-[1,1'-biphenyl]-3-yl)methylene)amino)-2-fluorophenoxy)acetic acid (I-22)

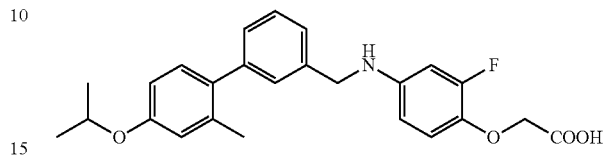

By substituting 3-methyl-4-bromophenol for the 3,5-dimethyl-4-bromophenol in Example 2, and substituting 2-bromopropane for the ethyl bromide in Example 2 Compound I-22 was prepared in a similar manner as in Example 2_to give a white solid (0.35 g, m.p. 134-137° C., yield 43%).

$^1$H NMR (300 MHz, DMSO-d$_6$) δ: 7.90-7.57 (m, 3H), 7.41 (d, J=6.8 Hz, 2H), 7.04 (s, 1H), 6.80 (d, J=6.8 Hz, 2H), 6.54 (s, 2H). 4.69 (m, J=8.9 Hz, 1H), 4.66 (s, 2H), 4.32 (s, 2H), 2.57 (s, 3H), 1.29 (d, J=8.9 Hz, 6H). $^{13}$C NMR (75 MHz, DMSO-d$_6$) δ: 169.9, 156.2, 152.9, 142.1, 141.5, 137.9, 136.3, 133.2, 128.7, 125.8, 125.2, 116.7, 113.7, 111.9, 111.4, 103.0, 75.8, 67.5, 48.3, 22.0, 19.0. ESI-MS m/z: 423.48 [M-H]$^-$. Anal. calcd. For C$_{25}$H$_{26}$FNO$_4$: C, 70.91; H, 6.19; N, 3.31; Found: C, 70.90; H, 6.18; N, 3.32.

Example 24

2-(4-((4'-isopropoxy-2'-methyl-[1,1'-biphenyl]-3-yl)methylene)amino)phenoxy)acetic acid (I-23)

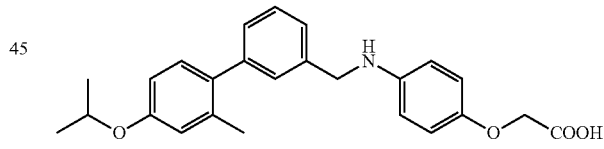

By substituting 4-nitrophenol for the 2-fluoro-4-nitrophenol in Example 1, substituting 3-methyl-4-bromophenol for the 3,5-dimethyl-4-bromophenol in Example 2_and substituting 2-bromopropane for the ethyl bromide of Example 2, Compound I-23 was prepared in a similar manner as in Example 2 to give a white solid (0.42 g, m.p. 132-135° C., yield 45%).

$^1$H NMR (300 MHz, DMSO-d$_6$) δ: 7.90-7.57 (m, 3H), 7.45 (s, 2H), 7.04 (s, 1H), 6.93 (s, 1H), 6.75 (s, 4H), 4.69 (m, J=8.9 Hz, 1H), 4.57 (s, 2H), 4.32 (s, 2H), 2.57 (s, 3H), 1.29 (d, J=8.9 Hz, 6H). $^{13}$C NMR (75 MHz, DMSO-d$_6$) δ: 169.9, 156.2, 146.5, 142.1, 141.6, 136.3, 133.3, 129.0, 128.7, 125.2, 115.1, 113.3, 111.9, 75.8, 64.7, 48.3, 22.0, 19.0. ESI-MS m/z: 405.19 [M-H]$^-$. Anal. calcd. For C$_{25}$H$_{27}$NO$_4$: C, 74.05; H, 6.71; N, 3.45; Found: C, 74.04; H, 6.70; N, 3.46.

Example 25

2-(4-((2'-chloro-[1,1'-biphenyl]-3-methylene)amino)phenoxy)acetic acid (I-24)

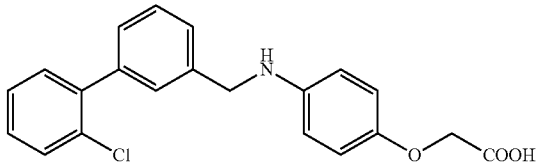 [SMILES: O=C(O)COc1ccc(NCc2cccc(-c3ccccc3Cl)c2)cc1]

By substituting 4-nitrophenol for the 2-fluoro-4-nitrophenol in Example 1, and substituting 2-chlorobromobenzene for the 3,5-dimethyl-4-bromophenol in Example 2, Compound I-24 was prepared in a similar manner as in Example 2 to give a white solid (0.49 g, m.p. 124-126° C., yield 51%).

$^1$H NMR (300 MHz, DMSO-d$_6$) δ: 12.91 (s, 1H), 7.71-7.41 (m, 5H), 7.38 (s, 2H), 6.77 (s, 2H), 6.73 (s, 2H), 6.54 (s, 1H), 4.57 (s, 2H), 4.32 (s, 2H). $^{13}$C NMR (75 MHz, DMSO-d$_6$) δ: 169.9, 146.5, 142.1, 141.6, 139.4, 136.3, 132.6, 128.7, 129.3, 129.0, 127.3, 125.8, 115.1, 113.3, 64.7, 48.3. ESI-MS m/z: 367.1 [M-H]$^-$. Anal. calcd. For C$_{21}$H$_{18}$ClNO$_3$: C, 68.57; H, 4.93; N, 3.81; Found: C, 68.56; H, 4.94; N, 3.81.

Example 26

2-(4-((2'-methyl-[1,1'-biphenyl]-3-methylene)amino)phenoxy)acetic acid (I-25)

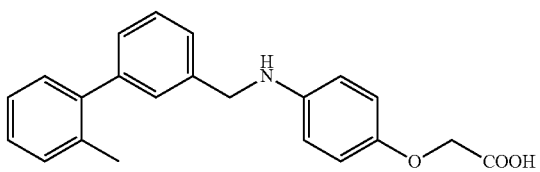 [SMILES: Cc1ccccc1-c1cccc(CNc2ccc(OCC(=O)O)cc2)c1]

By substituting 4-nitrophenol for the 2-fluoro-4-nitrophenol in Example 1, and substituting 2-methylbromobenzene for the 3,5-dimethyl-4-bromophenol in Example 2, Compound I-25 was prepared in a similar manner as in Example 2 to give a white solid (0.32 g, m.p. 101-104° C., yield 44%).

$^1$H NMR (300 MHz, DMSO-ds) δ:12.91 (s, 1H), 7.90-7.57 (m, 5H), 7.35 (s, 2H), 6.77 (s, 2H), 6.73 (s, 2H), 6.54 (s, 1H), 4.57 (s, 2H), 4.32 (s, 2H), 2.23 (s, 3H). $^{13}$C NMR (75 MHz, DMSO-d6) δ:169.9, 146.5, 142.1, 141.6, 136.3, 135.9, 133.6, 129.5, 129.0, 128.7, 127.5, 126.2, 125.6, 115.1, 113.3, 64.7, 48.3, 18.3. ESI-MS m/z: 347.15 [M-H]$^-$. Anal. calcd. For C$_{22}$H$_{21}$NO$_3$: C, 76.06; H, 6.09; N, 4.03; Found: C, 76.07; H, 6.08; N, 4.05.

Example 27

2-(4-((2'-fluoro-[1,1'-biphenyl]-3-methylene)amino)phenoxy)acetic acid (I-26)

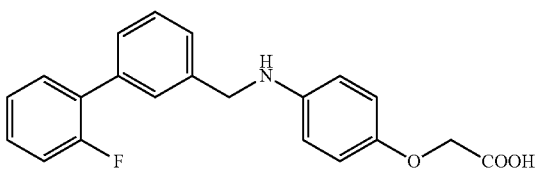

By substituting 4-nitrophenol for the 2-fluoro-4-nitrophenol in Example 1, and substituting 2-fluorobromobenzene for the 3,5-dimethyl-4-bromophenol in Example 2, Compound I-26 was prepared in a similar manner as in Example 2 to give a white solid (0.46 g, m.p. 111-112° C., yield 53%).

$^1$H NMR (300 MHz, DMSO-d$_6$) δ: 12.91 (s, 1H), 7.90-7.57 (m, 5H), 7.41 (s, 2H), 6.73 (s, 2H), 6.53 (s, 2H), 6.44 (s, 1H), 4.57 (s, 2H), 4.32 (s, 2H). $^{13}$C NMR (75 MHz, DMSO-d$_6$) δ:169.9, 158.7, 146.5, 142.1, 141.6, 136.3, 129.0, 125.9, 129.0, 124.8, 115.1, 114.7, 113.3, 64.7, 48.3. ESI-MS m/z: 347.15 [M-H]$^-$. Anal. calcd. For C$_{21}$H$_{18}$FNO$_3$: C, 71.78; H, 5.16; N, 3.99; Found: C, 71.79; H, 5.15; N, 4.00.

Example 28

2-(4-((2'-chloro-4'-methyl-[1,1'-biphenyl]-3-methylene)amino)phenoxy)acetic acid (I-27)

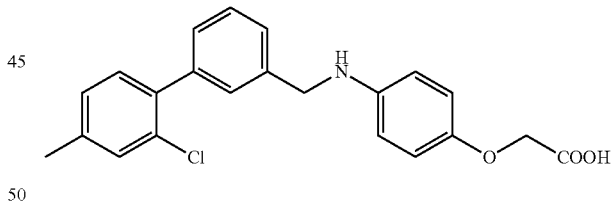

By substituting 4-nitrophenol for the 2-fluoro-4-nitrophenol in Example 1, and substituting 2-chloro-4-methylbromobenzene for the 3,5-dimethyl-4-bromo in Example 2. Compound I-27 was prepared in a similar manner as in Example 2 to give a white solid (0.38 g, m.p. 111-114° C., yield 46%).

$^1$H NMR (300 MHz, DMSO-d$_6$) δ: 12.91 (s, 1H), 7.90-7.57 (m, 4H), 7.41 (s, 2H), 7.14 (s, 2H), 6.73 (s, 2H), 6.64 (s, 1H), 4.57 (s, 2H), 4.32 (s, 2H), 2.36 (s, 3H). $^{13}$C NMR (75 MHz, DMSO-d$_6$) δ:172.9, 138.7, 136.4, 136.9, 132.5, 130.4, 129.7, 126.8, 127.6, 126.2, 129.0, 68.6, 67.5, 54.8, 45.4, 20.8 ESI-MS m/z: 381.11 [M-H]$^-$. Anal. calcd. For C$_{22}$H$_{20}$ClNO$_3$: C, 69.20; H, 5.28; N, 3.67; Found: C, 69.19; H, 5.27; N, 3.68.

Example 29

2-(4-((2'-trifluoromethyl-[1,1'-biphenyl]-3-methyl-ene)amino)phenoxy)acetic acid (I-28)

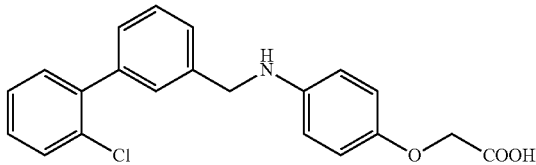 [SMILES: O=C(O)COc1ccc(NCc2cccc(-c3ccccc3Cl)c2)cc1]

By substituting 4-nitrophenol for the 2-fluoro-4-nitrophenol in Example 1, and substituting 2-trifluoromethylbromobenzene for the 3,5-dimethyl-4-bromophenol in Example 2, Compound I-28 was prepared in a similar manner as in Example 2 to give a white solid (0.39 g, m.p. 115-117° C., yield 63%).

$^1$H NMR (300 MHz, DMSO-$d_6$) δ: 12.91 (s, 1H), 7.90-7.66 (m, 5H), 7.33 (s, 2H), 7.14 (s, 2H), 6.77 (s, 2H), 6.64 (s, 1H), 4.57 (s, 2H), 4.32 (s, 2H), 2.36 (s, 3H). $^{13}$C NMR (75 MHz, DMSO-ds) δ: 169.9, 146.5, 142.1, 141.6, 136.3, 132.5, 129.7, 128.7, 127.9, 126.0, 125.6, 123.9, 115.1, 113.3, 64.7, 48.3. ESI-MS m/z: 401.12 [M-H]$^-$. Anal. calcd. For $C_{22}H_{18}F_3NO_3$: C, 65.83; H, 4.52; N, 3.49; Found: C, 65.83; H, 4.56; N, 3.48.

Example 30

2-(4-((4'-trifluoromethoxy-2',6'-dimethyl-[1,1'-biphenyl]-3-methylene)amino)phenoxy)acetic acid (I-29)

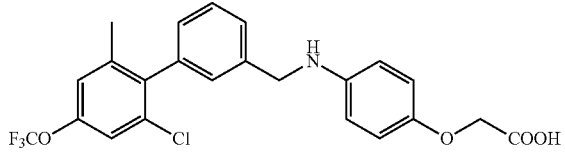 [SMILES: Cc1cc(OC(F)(F)F)cc(Cl)c1-c1cccc(CNc2ccc(OCC(=O)O)cc2)c1]

By substituting 4-nitrophenol for the 2-fluoro-4-nitrophenol in Example 1, and substituting 2,6-dimethyl-4-trifluoromethoxybromobenzene for 3,5-dimethyl-4-bromophenol in Example 2, Compound I-29 was prepared in a similar manner as in Example 2 to give a white solid (0.27 g, m.p. 117-120° C., yield 56%).

$^1$H NMR (300 MHz, DMSO-$d_6$) δ: 12.80 (s, 1H), 7.90 (s, 1H), 7.57-7.35 (m, 4H), 6.94 (s, 2H), 6.77 (s, 2H), 6.64 (s, 1H), 4.57 (s, 2H), 4.32 (s, 2H), 2.57 (s, 6H). $^{13}$C NMR (75 MHz, DMSO-$d_6$) δ: 169.9, 159.3, 146.5, 142.1, 141.6, 138.2, 136.3, 130.9, 129.7, 128.7, 125.8, 115.1, 113.3, 110.6, 64.7, 48.3, 19.3. ESI-MS m/z: 445.15 [M-H]$^-$. Anal. calcd. For $C_{24}H_{22}F_3NO_4$: C, 64.71; H, 4.98; N, 3.14; Found: C, 64.72; H, 4.97; N, 3.14.

Example 31

2-(4-((4'-trifluoromethoxy-2'-methyl-[1,1'-biphenyl]-3-methylene)amino)phenoxy)acetic acid (I-30))

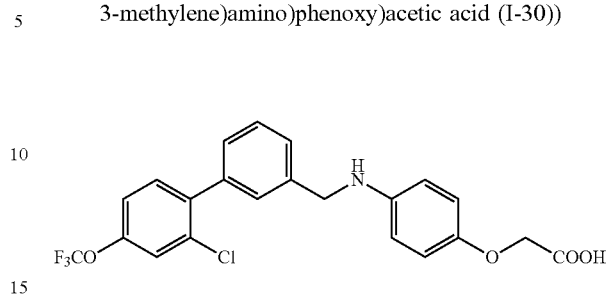

By substituting 4-nitrophenol for the 2-fluoro-4-nitrophenol in Example 1, and substituting 2-methyl-4-trifluoromethoxybromobenzene for the 3,5-dimethyl-4-bromophenol in Example 2, Compound I-30 was prepared in a similar manner as in Example 2 to give a white solid (0.33 g, m.p. 118-120° C., yield 43%).

$^1$H NMR (300 MHz, DMSO-$d_6$) δ: 12.80 (s, 1H), 7.90 (s, 1H), 7.72-7.35 (m, 4H), 7.04 (d, J=6.8 Hz, 2H), 6.93 (d, J=6.8 Hz, 1H), 6.77 (s, 2H), 6.64 (s, 1H), 4.57 (s, 2H), 4.32 (s, 2H), 2.57 (s, 3H). $^{13}$C NMR (75 MHz, DMSO-$d_6$) δ: 169.9, 159.4, 146.5, 142.1, 141.6, 136.3, 133.6, 129.7, 128.7, 125.9, 115.1, 113.1, 111.8, 64.7, 48.3, 19.0. ESI-MS m/z: 431.13 [M-H]$^-$. Anal. calcd. For $C_{23}H_{20}F_3NO_4$: C, 64.03; H, 4.67; N, 3.25; Found: C, 64.02; H, 4.67; N, 3.24.

Example 32

2-(4-(((4'-ethoxy-2'-methyl-[1,1'-biphenyl]-3-yl)methylene)amino)phenoxy)acetic acid (I-31)

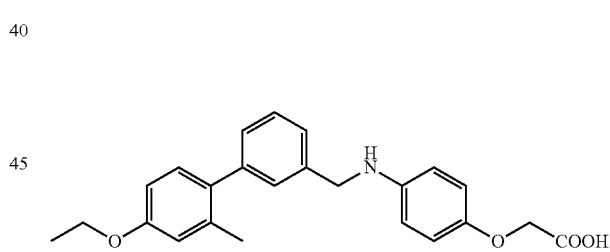

By substituting 4-nitrophenol for the 2-fluoro-4-nitrophenol in Example 1, and substituting 3-methyl-4-bromophenol for the 3,5-dimethyl-4-bromophenol in Example 2, Compound I-31 was prepared in a similar manner as in Example 2 to give a white solid (0.47 g, m.p. 121-124° C., yield 44%).

$^1$H NMR (300 MHz, DMSO-$d_6$) δ: 12.80 (s, 1H), 7.90 (s, 1H), 7.72-7.35 (m, 4H), 7.04 (d, J=6.8 Hz, 1H), 6.93 (d, J=6.8 Hz, 1H), 6.77 (s, 2H), 6.73 (s, 2H), 4.57 (s, 2H), 4.06 (q, J=8.9 Hz, 2H), 4.32 (s, 2H), 2.57 (s, 3H), 1.34 (t, J=8.9 Hz, 3H). $^{13}$C NMR (75 MHz, DMSO-$d_6$) δ: 169.9, 156.2, 146.5, 142.1, 141.6, 136.3, 133.2, 129.0, 128.7, 125.9, 125.3, 115.1, 113.3, 111.9, 64.7, 48.3, 19.0, 14.8. ESI-MS m/z: 391.47 [M-H]$^-$. Anal. calcd. For $C_{24}H_{24}NO_4$: C, 73.64; H, 6.44; N, 3.58; Found: C, 73.62; H, 6.45; N, 3.58.

Example 33

2-(4-((2'-trifluoromethoxy-[1,1'-biphenyl]-3-methylene)amino)phenoxy)acetic acid (I-32)

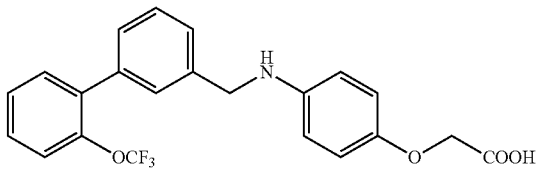

By substituting 4-nitrophenol for the 2-fluoro-4-nitrophenol in Example 1, and substituting 2-trifluoromethoxybromobenzene for the 3,5-dimethyl-4-bromophenol in Example 2, Compound i-32 was prepared in a similar manner as in Example 2 to give a white solid (0.34 g, m.p. 107-110° C., yield 45%).

$^1$H NMR (300 MHz, DMSO-$d_6$) δ: 12.80 (s, 1H), 7.99 (d, J=6.9 Hz, 1H), 7.90 (s, 1H), 7.57-7.41 (m, 4H), 7.14 (d, J=6.8 Hz, 2H), 6.77 (s, 2H), 6.73 (s, 2H), 4.57 (s, 2H), 4.32 (s, 2H). $^{13}$C NMR (75 MHz, DMSO-$d_6$) δ: 169.9, 157.7, 146.5, 142.1, 141.6, 136.3, 131.9, 130.8, 130.0, 128.7, 125.8, 121.5, 116.6, 115.1, 113.3, 64.6, 48.3. ESI-MS m/z: 417.12 [M-H]$^-$. Anal. calcd. For $C_{22}H_{18}F_3NO_4$: C, 63.31; H, 4.35; N, 3.36; Found: C, 63.32; H, 4.35; N, 3.38.

Example 34

2-(4-((2'-trifluoromethoxy-[1,1'-biphenyl]-3-methylene)amino-2-fluorophenoxy)acetic acid (I-33)

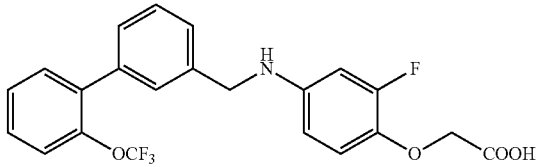 [SMILES: O=C(O)COc1ccc(NCc2cccc(-c3ccccc3OC(F)(F)F)c2)cc1F]

By substituting 2-trifluoromethoxybromobenzene for the 3,5-dimethyl-4-bromophenol of Example 2, Compound I-33 was prepared in a similar manner as in Example 2 to give a white solid (0.48 g, m.p. 111-113° C., yield 48%).

$^1$H NMR (300 MHz, DMSO-$d_6$) δ: 12.80 (s, 1H), 7.99 (d, J=6.9 Hz, 1H), 7.90 (s, 1H), 7.57-7.41 (m, 4H), 7.14 (d, J=6.8 Hz, 2H), 6.82 (s, 2H), 6.54 (s, 1H), 4.66 (s, 2H), 4.32 (s, 2H). $^{13}$C NMR (75 MHz, DMSO-$d_6$) δ: 169.9, 157.7, 152.9, 142.1, 141.5, 137.9, 136.3, 131.9, 130.8, 130.0, 129.0, 128.7, 125.8, 121.5, 116.7, 111.4, 103.0, 67.5, 48.3. ESI-MS m/z: 435.11 [M-H]$^-$. Anal. calcd. For $C_{22}H_{17}F_4NO_4$: C, 60.69; H, 3.94; N, 3.22; Found: C, 60.68; H, 3.95; N, 3.21.

Example 35

2-(4-((4'-trifluoromethoxy-2',6'-dimethyl-[1,1'-biphenyl]-3-methylene)amino)-2-fluorophenoxy)acetic acid (I-34)

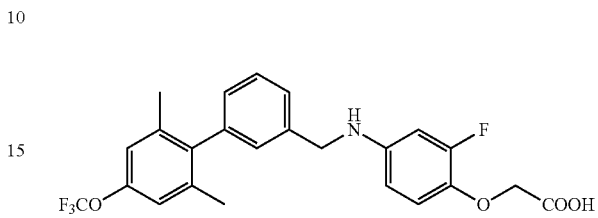

By substituting 2,6-dimethyl-4-trifluoromethoxybromobenzene for 3,5-dimethyl-4-bromophenol, Compound I-34 was prepared in a similar manner as in Example 2 to give a white solid (0.28 g, m.p. 127-130° C., yield 53%).

$^1$H NMR (300 MHz, DMSO-$d_6$) δ:12.80 (s, 1H), 7.90 (s, 1H), 7.57-7.41 (m, 3H), 6.94 (d, J=7.2 Hz, 2H), 6.84 (d, J=7.2 Hz, 1H), 6.77 (s, 1H), 6.54 (s, 1H), 4.66 (s, 2H), 4.32 (s, 2H), 2.57 (s, 6H). $^{13}$C NMR (75 MHz, DMSO-ds) δ: 169.9, 159.3, 152.9, 142.1, 141.5, 138.2, 137.9, 136.3, 130.9, 129.7, 128.7, 125.8, 116.7, 111.4, 110.6, 103.0, 67.5, 48.3, 19.3. ESI-MS m/z: 463.14 [M-H]$^-$. Anal. calcd. For $C_{24}H_{21}F_4NO_4$: C, 62.20; H, 4.57; N, 3.02; Found: C, 62.22; H, 4.56; N, 3.01.

Example 36

2-(4-((4'-trifluoromethoxy-2'-methyl-[1,1'-biphenyl]-3-methylene)amino)2-fluorophenoxy)acetic acid (I-35)

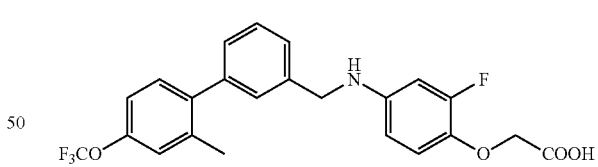

By substituting 2-methyl-4-trifluoromethoxybromobenzene for 2,5-dimethyl-4-bromophenol in Example 2, Compound I-35 was prepared in a similar manner as in Example 2 to give a white solid (0.41 g, m.p. 123-125° C., yield 43%).

$^1$H NMR (300 MHz, DMSO-$d_6$) δ: 12.80 (s, 1H), 7.90 (s, 1H), 7.72-7.41 (m, 5H), 7.04 (s, 1H), 6.93 (d, J=7.2 Hz, 1H), 6.84 (d, J=7.2 Hz, 1H), 6.77 (s, 1H), 6.54 (s, 1H), 4.66 (s, 2H), 4.32 (s, 2H), 2.57 (s, 3H). $^{13}$C NMR (75 MHz, DMSO-$d_6$) δ: 169.9, 159.4, 152.9, 142.1, 141.5, 137.9, 136.3, 133.6, 129.7, 128.7, 125.9, 116.7, 113.6, 111.8, 103.0, 67.5, 48.3, 19.0. ESI-MS m/z: 449.13 [M-H]$^-$. Anal. calcd. For $C_{23}H_{19}F_4NO_4$: C, 61.47; H, 4.26; N, 3.12; Found: C, 61.45; H, 4.26; N, 3.11.

Example 37

2-(2-fluoro-4-((4'-(2-ethoxyethoxy)-2',6'-dimethyl-[1,1'-biphenyl]-3-methylene)amino)phenoxy)acetic acid (I-36)

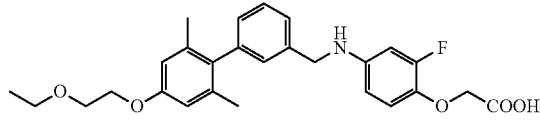 [SMILES: CCOCCOc1cc(C)c(-c2cccc(CNc3ccc(OCC(=O)O)c(F)c3)c2)c(C)c1]

By substituting bromoethanol for the bromoethane in Example 2, compound I-36 was prepared in a similar manner as in Example 2 to give a white solid (0.49 g, m.p. 137-139° C., yield 45%).

$^1$H NMR (300 MHz, DMSO-d$_6$) δ: 12.80 (s, 1H), 7.90 (s, 1H), 7.38-7.29 (m, 2H), 7.04 (s, 1H), 6.96 (d, J=7.2 Hz, 1H), 6.82 (d, J=7.2 Hz, 1H), 6.68 (s, 2H), 6.29 (s, 1H), 4.52 (s, 2H), 4.31 (t, J=3.4 Hz, 2H), 4.27 (s, 2H), 3.77 (t, J=3.4 Hz, 2H), 3.46 (q, J=4.5 Hz, 2H), 2.57 (s, 6H), 1.03 (t, J=4.5 Hz, 3H). $^{13}$C NMR (75 MHz, DMSO-d$_6$) δ: 169.9, 156.1, 152.9, 142.1, 141.5, 137.9, 136.3, 130.2, 128.7, 125.8, 116.7, 111.4, 110.7, 103.0, 69.3, 67.5, 66.6, 48.3, 19.3, 15.2. ESI-MS m/z: 467.21 [M-H]$^-$. Anal. calcd. For C$_{27}$H$_{30}$FNO$_5$: C, 69.36; H, 6.47; N, 3.00; Found: C, 69.35; H, 6.46; N, 3.01.

Example 38

2-(4-((4'-(2-ethoxyethoxy)-2',6'-dimethyl-[1,1'-biphenyl]-3-methylene)amino)phenoxy)acetic acid (I-37)

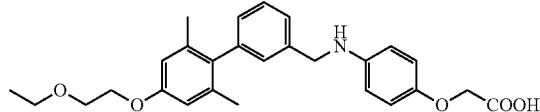 [SMILES: CCOCCOc1cc(C)c(-c2cccc(CNc3ccc(OCC(=O)O)cc3)c2)c(C)c1]

By substituting 4-nitrophenol for the 2-fluoro-4-nitrophenol in Example 1 with, and substituting bromoethanol for the ethyl bromide in Example 2, Compound I-37 was prepared in a similar manner as in Example 2 to give a white solid (0.29 g, m.p. 133-136° C., yield 46%).

$^1$H NMR (300 MHz, DMSO-d$_6$) δ: 12.80 (s, 1H), 7.90 (s, 1H), 7.57-7.41 (m, 3H), 6.94 (d, J=7.2 Hz, 2H), 6.77 (s, 2H), 6.73 (d, J=7.2 Hz, 2H), 4.52 (s, 2H), 4.31 (t, J=3.4 Hz, 2H), 4.27 (s, 2H), 3.77 (t, J=3.4 Hz, 2H), 3.46 (q, J=4.5 Hz, 2H), 2.57 (s, 6H), 1.05 (t, J=4.5 Hz, 3H). $^{13}$C NMR (75 MHz, DMSO-d$_6$) δ: 169.9, 156.1, 146.5, 142.1, 141.5, 137.8, 136.3, 130.2, 128.7, 125.8, 115.1, 113.3, 110.7, 69.3, 64.7, 66.6, 48.3, 19.3, 15.2. ESI-MS m/z: 449.22 [M-H]$^-$. Anal. calcd. For C$_{27}$H$_{31}$NO$_5$: C, 72.14; H, 6.95; N, 3.12; Found: C, 72.15; H, 6.96; N, 3.11.

Example 39

2-(2-fluoro-4-((4'-(2-methoxymethoxy)-2',6'-dimethyl-[1,1'-biphenyl]-3-methylene) amino)phenoxy)acetic acid (I-38)

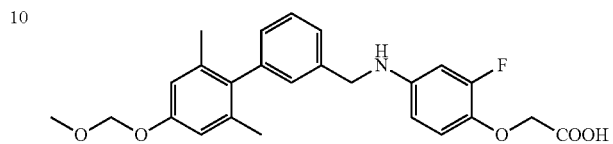

By substituting bromoethanol for the bromoethane in Example 2, Compound I-38 was prepared in a similar manner as in Example 2 to give a white solid (0.32 g, m.p. 136-138° C., yield 51%)

$^1$H NMR (300 MHz, DMSO-d$_6$) δ: 12.80 (s, 1H), 7.90 (s, 1H), 7.57-7.41 (m, 3H), 6.96 (d, J=7.2 Hz, 2H), 6.94 (d, J=7.2 Hz, 1H), 6.84 (s, 1H), 6.54 (s, 1H), 6.02 (s, 2H), 4.66 (s, 2H), 4.32 (s, 2H), 3.30 (s, 3H), 2.57 (s, 6H). $^{13}$C NMR (75 MHz, DMSO-d$_6$) δ: 169.9, 159.3, 152.9, 142.1, 141.5, 138.2, 137.9, 136.3, 130.9, 128.7, 125.8, 116.7, 111.4, 110.6, 103.0, 94.9, 67.5, 55.6, 48.3, 19.3. ESI-MS m/z: 439.18 [M-H]$^-$. Anal. calcd. For C$_{25}$H$_{26}$FNO$_5$: C, 68.32; H, 5.96; N, 3.19; Found: C, 68.31; H, 5.96; N, 3.18.

Example 40

2-(4-((4'-(2-methoxymethoxy)-2',6'-dimethyl-[1,1'-biphenyl]-3-methylene)amino)phenoxy)acetic acid (I-39)

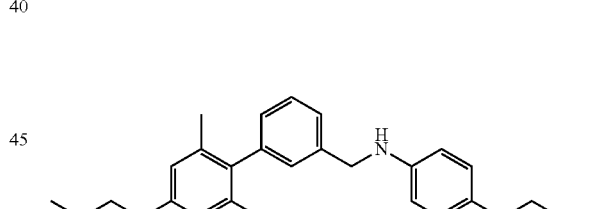

By substituting 4-nitrophenol for the 2-fluoro-4-nitrophenol in Example 1, and substituting bromoethanol for the ethyl bromide in Example 2, Compound I-39 was prepared in a similar manner as in Example 2 to give a white solid (0.42 g, m.p. 132-134° C., yield 57%).

$^1$H NMR (300 MHz, DMSO-d$_6$) δ: 12.80 (s, 1H), 7.90 (s, 1H), 0.57-7.41 (m, 3H), 6.94 (d, J=7.2 Hz, 2H), 6.77 (s, 2H), 6.73 (d, J=7.2 Hz, 2H), 6.02 (s, 2H), 4.66 (s, 2H), 4.32 (s, 2H), 3.30 (s, 3H), 2.57 (s, 6H). $^{13}$C NMR (75 MHz, DMSO-ds) δ: 169.9, 159.3, 146.5, 142.1, 141.6, 138.2, 136.3, 130.9, 128.7, 125.8, 115.1, 113.3, 110.6, 94.9, 64.7, 55.6, 48.3, 19.3. ESI-MS m/z: 421.19 [M-H]$^-$. Anal. calcd. For C$_{25}$H$_{27}$NO$_5$: C, 71.24; H, 6.46; N, 3.32; Found: C, 71.25; H, 6.46; N, 3.31.

Example 41

2-(2-fluoro-4-((4'-(2-ethoxymethoxy)-2',6'-dimethyl-[1,1'-biphenyl]-3-methylene)amino)phenoxy)acetic acid (I-40)

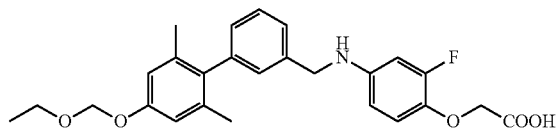 [SMILES: CCOCOc1cc(C)c(-c2cccc(CNc3ccc(OCC(=O)O)c(F)c3)c2)c(C)c1]

By substituting bromoethanol for bromoethane of Example 2, and Compound I-40 was prepared in a similar manner as in Example 2 to give a white solid (0.40 g, m.p. 136-139° C., yield 47%).

$^1$H NMR (300 MHz, DMSO-$d_6$) δ: 12.80 (s, 1H), 7.90 (s, 1H), 7.57-7.41 (m, 3H), 6.96 (d, J=7.2 Hz, 2H), 6.94 (d, J=7.2 Hz, 1H), 6.84 (s, 1H), 6.54 (s, 1H), 6.02 (s, 2H), 4.66 (s, 2H), 4.32 (s, 2H), 3.53 (q, J=5.6 Hz, 2H), 2.57 (s, 6H), 1.18 (t, J=5.6 Hz, 3H). $^{13}$C NMR (75 MHz, DMSO-$d_6$) δ: 169.9, 159.3, 152.9, 142.1, 141.5, 138.2, 137.9, 136.3, 130.9, 128.7, 125.8, 116.7, 111.4, 110.6, 103.0, 92.4, 67.5, 63.9, 48.3, 19.3, 15.2. ESI-MS m/z: 453.20 [M-H]$^-$. Anal. calcd. For $C_{26}H_{28}FNO_5$: C, 68.86; H, 6.22; N, 3.09; Found: C, 68.87; H, 6.23; N, 3.08.

Example 42

2-(4-((4'-(2-ethoxymethoxy)-2',6'-dimethyl-[1,1'-biphenyl]-3-methylene)amino)phenoxy)acetic acid (I-41)

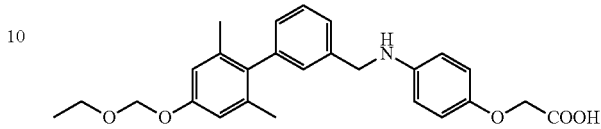

By substituting 4-nitrophenol for the 2-fluoro-4-nitrophenol in Example 1, and substituting bromoethanol for the ethyl bromide in Example 2, Compound I-41 was prepared in a similar manner as in Example 2 to give a white solid (0.40 g, m.p. 128-131° C., yield 54%).

$^1$H NMR (300 MHz, DMSO-$d_6$) δ: 12.80 (s, 1H), 7.90 (s, 1H), 7.57-7.41 (m, 3H), 6.94 (d, J=7.2 Hz, 2H), 6.77 (d, J=7.2 Hz, 2H), 6.73 (s, 2H), 6.02 (s, 2H), 4.66 (s, 2H), 4.32 (s, 2H), 3.53 (q, J=5.6 Hz, 2H), 2.57 (s, 6H), 1.18 (t, J=5.6 Hz, 3H). $^{13}$C NMR (75 MHz, DMSO-$d_6$) δ: 169.9, 159.3, 146.5, 142.1, 141.6, 138.2, 136.3, 130.9, 128.7, 125.8, 115.1, 113.3, 110.6, 92.4, 64.7, 63.9, 48.3, 19.3, 15.2. ESI-MS m/z: 435.20 [M-H]$^-$. Anal. calcd. For $C_{26}H_{29}NO_5$: C, 71.70; H, 6.71; N, 3.22; Found: C, 71.69; H, 6.72; N, 3.22.

Example 43

2(2-fluoro-4-(((4'-(hexyloxy)-2',6'-dimethyl-[1,1'-biphenyl]-3-yl)methyl)amino)phenoxy)acetic acid (I-42)

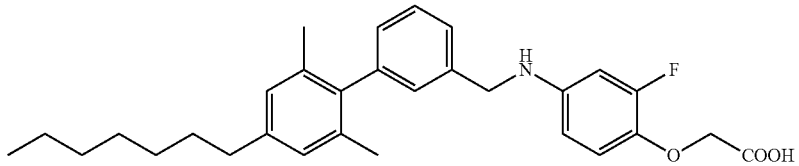 [SMILES: CCCCCCCc1cc(C)c(-c2cccc(CNc3ccc(OCC(=O)O)c(F)c3)c2)c(C)c1]

By substituting 1-bromohexane for the ethyl bromide in Example 2, Compound I-42 was prepared in a similar manner as in Example 2 to give a white solid (0.60 g, m.p. 132-135° C. and yield 45%).

$^1$H NMR (300 MHz, DMSO-$d_6$) δ: 12.80 (s, 1H), 7.90 (s, 1H), 7.57-7.41 (m, 3H), 6.94 (d, J=7.2 Hz, 2H), 6.77 (d, J=7.2 Hz, 1H), 6.73 (s, 2H), 4.66 (s, 2H), 4.32 (s, 2H), 4.06 (t, J=5.6 Hz, 2H), 2.57 (s, 6H), 1.80 (m, 2H), 1.47 (m, 2H), 1.37 (m, 4H), 0.88 (t, t, J=5.2 Hz, 3H). $^{13}$C NMR (75 MHz, DMSO-$d_6$) δ:169.9, 156.1, 152.9, 142.1, 141.5, 137.9, 136.3, 130.2, 128.7, 125.8, 116.7, 111.4, 110.7, 103.0, 68.7, 67.5, 48.3, 31.8, 29.6, 25.6, 22.7, 19.3, 14.1. ESI-MS m/z: 479.25 [M-H]$^-$. Anal. calcd. For $C_{29}H_{34}FNO_4$: C, 72.63; H, 7.15; N, 2.92; Found: C, 72.62; H, 7.14; N, 2.92.

Example 44

2(4-(((4'-(hexyloxy)-2',6'-dimethyl-[1,1'-biphenyl]-3-yl)methyl)amino)phenoxy)acetic acid (I-43)

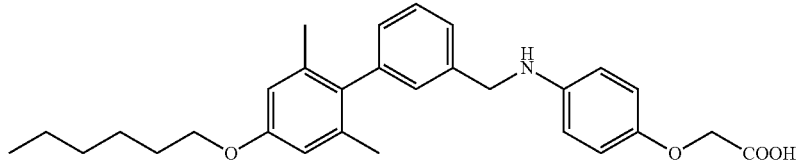 [SMILES: CCCCCCOc1cc(C)c(-c2cccc(CNc3ccc(OCC(=O)O)cc3)c2)c(C)c1]

By substituting 1-bromohexane for the ethyl bromide in Example 2, and substituting 4-nitrophenol for the 2-fluoro-4-nitrophenol in Example 1, Compound I-43 was prepared in a similar manner as in Example 2 to give a white solid (0.64 g, m.p. 130-132° C., yield 49%).

$^1$H NMR (300 MHz, DMSO-d$_6$) δ: 12.80 (s, 1H), 7.90 (s, 1H), 7.57-7.41 (m, 3H), 6.94 (d, J=7.2 Hz, 2H), 6.77 (d, J=7.2 Hz, 2H), 6.73 (s, 2H), 4.66 (s, 2H), 4.32 (s, 2H), 4.06 (t, J=5.6 Hz, 2H), 2.57 (s, 6H), 1.80 (m, 2H), 1.47 (m, 2H), 1.37 (m, 4H), 0.88 (t, t, J=5.2 Hz, 3H). $^{13}$C NMR (75 MHz, DMSO-d$_6$) δ:169.9, 156.1, 152.9, 142.1, 141.5, 137.9, 136.3, 130.2, 128.7, 125.8, 116.7, 113.1, 111.4, 110.7, 103.0, 68.7, 64.7, 48.3, 31.8, 29.6, 25.6, 22.7, 19.3, 14.1. ESI-MS m/z: 461.26 [M-H]$^-$. Anal. calcd. For C$_{29}$H$_{35}$NO$_4$: C, 75.46; H, 7.64; N, 3.03; Found: C, 75.45; H, 7.64; N, 3.02.

Example 45

2(2-fluoro-4-(((4'-(cyclohexyloxy)-2',6'-dimethyl-[1,1'-biphenyl]-3-yl)methyl)amino)phenoxy)acetic acid (I-44)

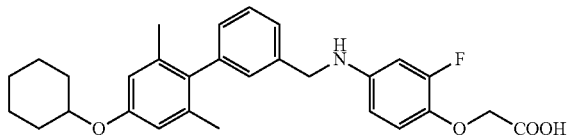 [SMILES: Cc1cc(OC2CCCCC2)cc(C)c1-c1cccc(CNc2ccc(OCC(=O)O)c(F)c2)c1]

By substituting 1-bromocyclohexane for the bromoethane of Example 2, Compound I-44 was prepared in a similar manner as in Example 2 to give a white solid (0.52 g, m.p. 136-138° C. and yield 49%).

$^1$H NMR (300 MHz, DMSO-d$_6$) δ: 12.80 (s, 1H), 7.90 (s, 1H), 7.57-7.35 (m, 3H), 6.94 (d, J=7.2 Hz, 2H), 6.77 (d, J=7.2 Hz, 1H), 6.73 (s, 2H), 4.66 (s, 2H), 4.32 (s, 2H), 3.64 (m, 1H), 2.57 (s, 6H), 1.95, 1.70 (dd, J=5.8 Hz, 2H), 1.53, 1.43 (dd, J=5.5 Hz, 2H), 1.46, 1.44 (dd, J=5.1 Hz, 2H). $^{13}$C NMR (75 MHz, DMSO-d$_6$) δ:169.9, 156.1, 152.9, 142.1, 141.5, 137.9, 136.3, 130.2, 128.7, 125.8, 116.7, 111.4, 110.7, 103.0, 78.0, 67.5, 48.3, 33.9, 26.0, 24.2, 19.3. ESI-MS m/z: 477.23 [M-H]$^-$. Anal. calcd. For C$_{29}$H$_{32}$FNO$_4$: C, 72.93; H, 6.75; N, 2.93; Found: C, 72.94; H, 6.74; N, 2.92.

Example 46

2(4-((4'-(cyclohexyloxy)-2',6'-dimethyl-[1,1'-biphenyl]-3-yl)methyl)amino)phenoxy)acetic acid (I-45)

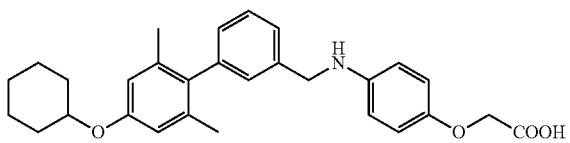 [SMILES: Cc1cc(OC2CCCCC2)cc(C)c1-c1cccc(CNc2ccc(OCC(=O)O)cc2)c1]

By substituting 1-bromocyclohexane for the ethyl bromide in Example 2, and substituting 4-nitrophenol for the 2-fluoro-4-nitrophenol in Example 1, Compound I-45 was prepared in a similar manner as in Example 2 to give a white solid (0.52 g, m.p. 136-138, yield 49%).

$^1$H NMR (300 MHz, DMSO-d$_6$) δ: 12.80 (s, 1H), 7.90 (s, 1H), 7.57-7.35 (m, 3H), 6.94 (d, J=7.2 Hz, 2H), 6.77 (d, J=7.2 Hz, 2H), 6.73 (s, 2H), 4.66 (s, 2H), 4.32 (s, 2H), 3.64 (m, 1H), 2.57 (s, 6H), 1.95, 1.70 (dd, J=5.8 Hz, 2H), 1.53, 1.43 (dd, J=5.5 Hz, 2H), 1.46, 1.44 (dd, J=5.1 Hz, 2H). $^{13}$C NMR (75 MHz, DMSO-d$_6$) δ:169.9, 156.1, 152.9, 146.5, 142.1, 141.6, 137.8, 136.3, 130.2, 128.7, 125.8, 115.1, 113.3, 110.7, 78.0, 64.7, 48.3, 33.9, 26.0, 24.2, 19.3. ESI-MS m/z: 459.24 [M-H]$^-$. Anal. calcd. For C$_{29}$H$_{33}$FNO$_4$: C, 75.79; H, 7.24; N, 3.05; Found: C, 75.78; H, 7.24; N, 3.04.

Example 47

Tablets containing any of the compounds of the invention:

| Each tablet contains (mg) | |
| --- | --- |
| any of the compounds of the invention (Examples 2-46) | 15 mg |
| microcrystalline cellulose | 80 mg |
| pregelatinized starch | 40 mg |
| polyvinylpyrrolidone | 8 mg |
| sodium carboxymethyl starch | 6 mg |
| magnesium stearate | 1.5 mg |
| talc powder | 2.5 mg |
| ethanol | appropriate amount |

The active ingredient, pregelatinized starch and microcrystalline cellulose were sieved, thoroughly mixed. A solution of polyvinylpyrrolidone was added and mixed to make the mixture into soft materials. After sieving, wet granules were prepared, dried at 50-60° C., and sodium carboxymethyl starch, magnesium stearate and talc powder were sieved and added to the above granules for tableting.

The above composition has also been confirmed to have excellent in vivo hypoglycemic activity.

What is claimed is:

1. A compound is selected from the group consisting of
2-(4-((2'-chloro-[1,1'-biphenyl]-3-methylene)amino)-2-fluorophenoxy)acetic acid (I-2),
2-(4-((2'-methoxy-[1,1'-biphenyl]-3-methylene)amino)-2-fluorophenoxy)acetic acid (I-6),
2-(4-((2'-nitrile-[1,1'-biphenyl]-3-methylene)amino)-2-fluorophenoxy)acetic acid (I-7),
2-(4-((2'-trifluoromethyl-[1,1'-biphenyl]-3-methylene)amino)-2-fluorophenoxy)acetic acid (I-8),
2-(4-(([1,1'-biphenyl]-3-methylene)amino)-2-fluorophenoxy)acetic acid (I-11),
2-(4-((2'-chloro-[1,1'-biphenyl]-3-methylene)amino)phenoxy)acetic acid (I-24),
2-(4-((2'-trifluoromethyl-[1,1'-biphenyl]-3-methylene)amino)phenoxy)acetic acid (I-28),
2-(4-((4'-trifluoromethoxy-2',6'-dimethyl-[1,1'-biphenyl]-3-methylene)amino)phenoxy)acetic acid (I-29),
2-(4-(((4'-ethoxy-2'-methyl-[1,1'-biphenyl]-3-yl)methylene)amino)phenoxy)acetic acid (I-31),
2-(4-((2'-trifluoromethoxy-[1,1'-biphenyl]-3-methylene)amino)phenoxy)acetic acid (I-32),
2-(4-((2'-trifluoromethoxy-[1,1'-biphenyl]-3-methylene)amino-2-fluoro)phenoxy)acetic acid (I-33),
2-(4-((4'-trifluoromethoxy-2',6'-dimethyl-[1,1'-biphenyl]-3-methylene)amino)-2-fluorophenoxy)acetic acid (I-34),
2(4-(((4'-(hexyloxy)-2',6'-dimethyl-[1,1'-biphenyl]-3-yl)methyl)amino)phenoxy)acetic acid (I-43), and
2(4-(((4'-(cyclohexyloxy)-2',6'-dimethyl-[1,1'-biphenyl]-3-yl)methyl)amino)phenoxy)acetic acid (I-45).

2. A pharmaceutical composition for treating diabetes and metabolic syndrome, comprising the compound according to claim 1, and suitable carriers or excipients.

* * * * *